United States Patent [19]

Kawai et al.

[11] Patent Number: 4,962,030
[45] Date of Patent: Oct. 9, 1990

[54] ALKALINE CELLULASES AND MICROORGANISMS CAPABLE OF PRODUCING SAME

[75] Inventors: Shuji Kawai, Utsunomiya; Kazushi Oshino, Koshigaya; Hiromi Okoshi, Utsunomiya; Hajime Mori, Utsunomiya; Katsuya Ozaki, Utsunomiya; Shitsuw Shikata, Utsunomiya; Susumu Ito, Utsunomiya; Kikuhiko Okamoto, Koshigaya, all of Japan

[73] Assignee: KAO Corporation, Tokyo, Japan

[21] Appl. No.: 126,005

[22] Filed: Nov. 27, 1987

[30] Foreign Application Priority Data

| Nov. 27, 1986 | [JP] | Japan | 61-282970 |
| Nov. 28, 1986 | [JP] | Japan | 61-283742 |
| Nov. 28, 1986 | [JP] | Japan | 61-283743 |
| Nov. 28, 1986 | [JP] | Japan | 61-283744 |
| Mar. 12, 1987 | [JP] | Japan | 62-57644 |
| Mar. 20, 1987 | [JP] | Japan | 62-67442 |
| Mar. 23, 1987 | [JP] | Japan | 62-68597 |
| Aug. 3, 1987 | [JP] | Japan | 62-194142 |
| Aug. 3, 1987 | [JP] | Japan | 62-194143 |
| Aug. 3, 1987 | [JP] | Japan | 62-194140 |

[51] Int. Cl.$^5$ .................... C12N 9/42; C12R 1/07
[52] U.S. Cl. .................. 435/209; 435/252.5; 435/832
[58] Field of Search ............. 435/209, 252.5, 832

[56] References Cited

U.S. PATENT DOCUMENTS 3,844,890 10/1974 Horikoshi et al. .................. 435/832
3,983,002 9/1976 Ohya et al. ........................ 435/822

FOREIGN PATENT DOCUMENTS 0271004 6/1988 European Pat. Off.

OTHER PUBLICATIONS

Sippola et al., "Coproduction of Several Exoenzymes in *Bacillus subtilis*," FEMS Microbiol. Lett., vol. 10, No. 4, pp. 303–306, 1981.
Chemical Abstracts, vol. 101, 1984, p. 334, Abstract No. 87124u.
Chemical Abstracts, vol. 103, 1985, p. 735, Abstract No. 213316q.
Agricultural Biol. Chem., vol. 50(1), Jan. 1986, pp. 233–237.
Microbiology Abstracts, B., vol. 10, No. 7, Jul. 1975, Abstract No. 10B7325, p. 41.
Chemical Abstracts, vol. 104, 1986, p. 312, Abstract No. 64633g.

*Primary Examiner*—Robert A. Wax
*Attorney, Agent, or Firm*—Oblon, Spivak, McClelland, Maier & Neustadt

[57] ABSTRACT

Alkaline cellulases having an optimum pH in an alkaline range and being stable over a broad pH range are produced by microorganisms which belong to the genus Bacillus and grow in a neutral medium.

These alkaline cellulases are rarely inhibited by ingredients ordinarily incorporated in detergents such as surface active agents, proteinases and chelating agents, so that they can be conveniently used in detergent compositions.

14 Claims, 17 Drawing Sheets

ALKALINE CELLULASES AND MICROORGANISMS CAPABLE OF PRODUCING SAME

BACKGROUND OF THE INVENTION

1. Field of the Invention

This invention relates to novel alkaline cellulases and also to microorganisms which are able to produce the same, belong to the genus Bacillus, and grow up in a neutral medium.

2. Description of the Prior Art

The development of cellulases, which are cellulose-decomposing enzymes, has been made for the purpose of effectively utilizing biomass resources and particularly, cellulose resources. A diversity of strains have been isolated as cellulase-producing fungi or bacteria including, for example, not only molds of the genera Aspergillus, Penicillium, Trichoderma, Fusarium, Humicola, Acremonium and the like, but also bacteria of the genera Pseudomonas, Cellulomonas, Ruminococcus, Bacillus and the like and actinomycetes of the genera Streptomyces, Thermoactinomyces and the like. At present, however, cellulases for biomass have not been frequently utilized on an industrial scale.

On the other hand, studies have been made on novel industrial utility of cellulases as an ingredient for detergents for clothes, to which attention has now been paid (Japanese Patent Publication Nos. 59-49279, 60-23158 and 60-36240). Most cellulases produced by microorganisms in the natural fields are classified as so-called neutral or acidic cellulases which exhibit optimum and stable enzymatic activity in a neutral to acidic range. Only a few cellulases are so-called alkaline cellulases which meet the requirements for formulation in detergent compositions for clothes or can exhibit an maximum activity in an alkaline pH range, and so-called alkali-resistant cellulases which have an alkali resistance. The term "alkaline cellulase" used herein is intended to mean one whose optimum pH is in an alkaline range, and the term "alkali-resistant cellulase" means one whose optimum pH is in a neutral or an acidic range, but which has a satisfactory activity as compared with an activity at an optimum pH and is maintained stable in an alkaline range. The term "neutral" means a pH range of from 6 to 8, and the term "alkaline" means a higher pH range.

For the production of alkaline cellulases and alkali-resistant cellulases usable in detergent compositions for clothes, only several methods have been proposed. These methods include, for example, a method of collecting cellulase A by cultivation of alkalophilic bacilli belonging to the genus Bacillus (Japanese Patent Publication No. 50-28515), a method of producing alkaline cellulase 301-A by cultivation of alkalophilic bacteria belonging to the genus Cellulomonas (Japanese Patent Application Laid-open No. 58-224686), a method of producing carboxymethyl cellulase by cultivation of alkalophilic Bacillus No. 1139 (Fukumori, F., Kudo T. and Horikoshi, K., J. Gen. Microbiol., 131, 3339, (1985)), and a method of producing an alkaline cellulase by the use of one strain belonging to the genus Streptomyces (Japanese Patent Application Laid-open No. 61-19483). However, these methods are all unsuitable for the industrial fermentation production.

In recent years, we have found that Bacillus sp. KSM-635 (FERM P-8872), which is one of alkalophilic bacteria, can efficiently product alkaline cellulase K which is suitable as an ingredient for detergents for clothes and that proper selection of cultivation conditions enables one to enhance the productivity and conduct industrial fermentation production of the alkaline cellulase.

However, the cultivation conditions of the Bacillus sp. KSM-635 are not always advantageous from an industrial point of view. More particularly, an alkalophilic strain should be cultivated under alkaline pH conditions during the cultivation. A so-called alkaline fermentation process using alkalophilic strains has just been started, and a full knowledge on the physiological and biochemical properties of these alkalophilic microorganisms has not been obtained. Thus, difficulties have been involved in the preparation of media and the manner of cultivation sufficient to effect the industrial production by fermentation.

Moreover, the true alkaline cellulases of the afore-described documents which have an optimum pH in an alkaline region, are enzymes which are produced by Bacillus N1 strain, N2 strain and N3 strain (Japanese Patent Publication No. 50-28515) and have optimum pHs of 8 to 9, 9 and 8 to 9, respectively, an enzyme produced by Bacillus No. 1139 and having an optimum pH of 9, and alkaline cellulase K produced by Bacillus sp. KSM-635 and having an optimum pH of 10 (Japanese Patent Application No. 61-257776). Now, there is a demand for alkaline cellulase which have an optimum pH in an alkaline region and can be suitably formulated in detergent compositions and which have a wide working pH range.

SUMMARY OF THE INVENTION

Under these circumstances, the present inventors made extensive studies in order to obtain strains which grow in neutral media and are capable of producing alkaline cellulases having good effects.

In order to solve the prior art problems, a gene recombination technique may be used in which a strain which grows up in a neutral region is employed as a host and corresponding cellulase genes are cloned. In this connection, however, it is more effective to search for neutral microorganism, in the natural field, which is able to produce an alkaline cellulase having an optimum pH in an alkaline region and to isolate it. Accordingly, the present inventors have sought such a microorganism in the natural field and, as a result, found that a series of microorganisms belonging to the genus Bacillus grow in neutral media and produce certain types of alkaline cellulases.

Typical alkaline cellulases according to the invention have the following enzymatic properties:

(1) having a broad optimum pH range of from 8 to 10 with a maximum activity at pH of approximately 10;

(2) the activity being inhibited by the presence of $Hg^{2+}$;

(3) the activity being rarely inhibited with proteinases, surface active agents and chelating agents; and (4) having the CMCase activity (Cx activity) as a main activity with additional filter paper-disintegrating activity and Avicelase activity ($C_1$ activity).

DETAILED DESCRIPTION OF THE INVENTION AND PREFERRED EMBODIMENTS

Figure 1:
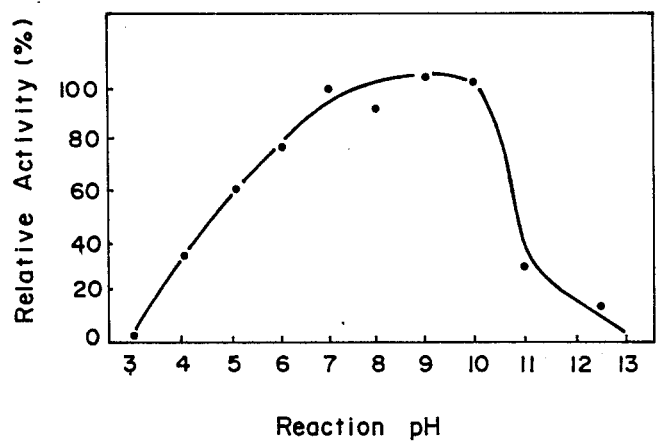
FIG. 1 is a graph showing the relation between a pH for the enzyme reaction of alkaline cellulase K-580 and a relative activity.

Examples of the microorganisms capable of producing the alkaline cellulases of the invention include strains isolated from the soils of Haga-gun and Nikko-shi in Tochigi, Japan.

These strains have the following mycological properties. It will be noted that the classification of the strains is carried out using the following medium Nos. 1 to 25 (in which values are by wt %).

Medium 1: meat extract, 1.0; Bacto peptone, 1.0; NaCl, 0.5; Bacto agar, 1.5 (pH 7.2)

Medium 2: meat extract, 1.0; Bacto peptone, 1.0; NaCl, 0.5 (pH 7.2)

Medium 3: meat extract, 1.0; Bacto peptone, 1.0; NaCl, 0.5; gelatin, 1.0 (pH 7.2)

Medium 4: Bacto litmus milk, 10.0

Medium 5: Bacto peptone, 1.0; $KNO_3$, 0.1

Medium 6: Bacto peptone, 1.0; $NaNO_3$, 0.1

Medium 7: Bacto peptone, 0.7; NaCl, 0.5; glucose, 0.5 (pH 7.0)

Medium 8: Bacto peptone, 1.0

Medium 9: TSI agar (by Eiken Chem. Co., Ltd., Japan), indicated amount

Medium 10: meat extract, 1.0; Bacto peptone, 1.0; NaCl, 0.5; soluble starch, 0.2; agar, 1.5

Medium 11: $NaNH_4HPO_4.4H_2O$, 0.15; $KH_2PO_4$, 0.1; $MgSO_4.7H_2O$, 0.02; sodium citrate, 0.25 (pH 6.8)

Medium 12: Christensen's medium (Eiken Chem. Co., Ltd., Japan), indicated amount Medium 13: glucose, 1.0; $KH_2PO_4$, 0.1; $MgSO_4.7H_2O$, 0.05; KCl, 0.02; nitrogen sources, 0.1 (pH 7.2)

The nitrogen sources used were sodium nitrate and ammonium sulfate.

Medium 14: King A medium "Eiken" (Eiken Chem. Co., Ltd., Japan), indicated amount Medium 15: King B medium "Eiken" (Eiken Chem. Co., Ltd., Japan), indicated amount Medium 16: urea medium "Eiken" (Eiken Chem. Co., Ltd., Japan), indicated amount Medium 17: filter paper for cytochrome oxidase test (Nisshui Pharm Co., Ltd., Japan)

Medium 18: 3% hydrogen peroxide aqueous solution

Medium 19: OF basal medium (Difco Lab.), indicated amount

Medium 20: $(NH_4)_2HPO_4$, 0.1; KCl, 0.02; $MgSO_4.7H_2O$, 0.02; yeast extract, 0.02; Bacto agar, 2.0; BCP (0.2% solution), 0.4

Medium 21: Bacto Sabouraud's dextrose agar medium (Difco Lab.), indicated amount Medium 22: meat extract, 0.3; Bacto peptone, 0.5; yeast extract, 1.0; glycerin, 2.0

Medium 23: phenyl alanine malonic acid salt medium (Nisshui Pharm Co., Ltd., Japan), indicated amount Medium 24: skim milk, 5.0; Bacto agar, 1.5

Medium 25: meat extract, 0.3; Bacto peptone, 0.5; L-tyrosine, 0.5; Bacto agar, 1.5

(Mycological properties)

Bacillus sp. KSM-580

(a) Bacillus sp. KSM-580 has a size of the body of 0.4–0.8 micrometers × 1.5–5.0 micrometers, and has a cylindrical or elliptical endospore (0.4–0.8 micrometers × 0.8–1.2 micrometers) at the terminal of the body. The bacillus has marginal flagellas and is mobile. The Gram's staining is positive. Not aciduric (b) Growing State in Various Media:

(1) Meat broth agar plate culture (medium 1)

The growing state is weak The shape of the colonies is in a round or irregular form with a smooth surface and a smooth or leaf-like margin. The color tone of the colonies is light yellow, semi-transparent and glossy.

(2) Meat broth agar slant culture (medium 1)

The growth is weak with the state being in a cloth-spreading form and being glossy, light yellow in color and semi-transparent.

(3) Meat broth liquid culture (medium 2) Growing. Especially, the upper layer becomes turbid.

(4) Meat broth gelatin stab culture (medium 3)

Growing in the surface layer with the gelatin being liquefied.

(5) Litmus milk medium (medium 4)

The liquefaction of the milk is recognized. The litmus does not change its color.

(c) Physiological properties:

(1) The reduction and denitrification reactions of nitrates (media 5 and 6) are both negative.

(2) MR test (medium 7)

Whether the test is negative or positive is not clear (pH 5.2).

(3) VP test (medium 7)

Whether the test is negative or positive is not clear (pH 5.2).

(4) Formation of indole (medium 8)

Negative.

(5) Formation of hydrogen sulfide (medium 9)

Negative.

(6) Hydrolysis of starch (medium 10)

Positive.

(7) Utility of citric acid (media 11, 12) Negative in a Koser's medium and positive in a Christensen's medium.

(8) Utility of inorganic nitrogen sources (medium 13)

Positive with respect to the nitrate and ammonium salt.

(9) Formation of pigment (media 14, 15)

Negative.

(10) Urease (medium 16)

Negative.

(11) Oxidase (medium 17)

Positive.

(12) Catalase (medium 18)

Positive.

(13) Temperature and pH ranges for growth (medium 2)

The temperature range for growth is 15°–50° C. and an optimum temperature range is 25°–40° C.

The pH range for the growth is 5–11 and an optimum pH range is 6–10.

(14) Behavior to oxygen

Facultatively anaerobic.

(15) O-F test (medium 19)

Although growing up, the growth is poor either aerobically or anaerobically.

(16) Utility of sugars (+: utilizing. −: not utilizing)

| | | |
|---|---|---|
| 1. L-arabinose | + | |
| 2. D-xylose | + | |
| 3. D-glucose | + | |
| 4. D-mannose | + | |
| 5. fructose | + | |
| 6. D-galactose | + | |
| 7. maltose | + | |
| 8. sucrose | + | |
| 9. lactose | + | |
| 10. trehalose | − | |

-continued

| | | |
|---|---|---|
| 11. D-sorbitol | + | |
| 12. D-mannitol | + | |
| 13. inositol | + | |
| 14. glycerin | + | |
| 15. starch | + | |

(17) pH in VP medium (medium 7)

pH 5.2

(18) Growth in a salt-containing medium (modified medium 1)

Growing at 5%.

Growing at 7%.

Not growing at 10%.

(19) Growth at a pH of 5.7 (medium 21)

Growing.

(20) Formation of dihydroxyacetone (medium 22)

Negative.

(21) Deamination of phenylalanine (medium 23)

Negative.

(22) Decomposition of casein (medium 24)

Positive.

(23) Decomposition of tyrosine (medium 25)

Negative.

Bacillus sp. KSM-425:

(a) Results of microscopic observation

Bacillus sp. KSM-425 has a size of the body of 0.4–0.8 micrometers × 1.5–4.0 micrometers, making an ellipsoidal endospore (0.8–1.2 micrometers × 1.2–1.5 micrometers) at one end of the body. It has marginal flagella and is mobile. The Gram staining is indefinite. Not aciduric (b) Growing state in various media (1) Meat broth agar plate culture (medium 1)

The growing state is poor. The shape of the colonies is circular with a smooth surface and a smooth margin. The color tone of the colonies is white, and the colonies are semi-transparent and glossy.

(2) Meat broth agar slant culture (medium 1)

The growth is poor and its state is in a cloth-spread form and is glossy, white in color and semi-transparent.

(3) Meat broth liquid culture (medium 2)

Growing and becoming turbid.

(4) Meat broth gelatin stab culture (medium 3)

Growing but in a poor state. The liquefaction of gelatin is not recognized.

(5) Litmus milk culture (medium 4)

The coagulation and liquefaction of milk is not recognized. The litmus does not undergo any change in color.

(c) Physiological properties (1) Reduction and denitrification reactions of nitrates (media 5, 6)

Both negative.

(2) MR test (medium 7)

Whether the test is negative or positive is not clear (pH 5.2).

(3) VP test (medium 7)

Negative (pH 5.2).

(4) Formation of indole (medium 8)

Negative.

(5) Formation of hydrogen sulfide (medium 9)

Negative.

(6) Hydrolysis of starch (medium 10)

Positive.

(7) Utility of citric acid (media 11, 12)

Negative both in a Koser's medium and in Christensen's medium.

(8) Utility of inorganic nitrogen sources (medium 13)

Negative with respect to the nitrate and ammonium salt.

(9) Formation of pigment (media 14, 15)
Negative.
(10) Urease (medium 16)
Negative.
(11) Oxidase (medium 17)
Positive.
(12) Catalase (medium 18)
Positive.
(13) Temperature and pH ranges for growth (medium 2)

The temperature range for the growth is 15°–37° C. and an optimum temperature range is 25°–30° C.

The pH range for the growth is 5–10 and an optimum pH range is 6–9.

(14) Behavior to oxygen
Facultatively anaerobic.
(15) O–F test (medium 19)
Although growing up, the growth is poor either aerobically or anaerobically.
(16) Utility of sugars (+: utilizng, −: not utilizing)

|  |  |
| --- | --- |
| 1. L-arabinose | + |
| 2. D-xylose | + |
| 3. D-glucose | + |
| 4. D-mannose | + |
| 5. fructose | + |
| 6. D-galactose | + |
| 7. maltose | + |
| 8. sucrose | + |
| 9. lactose | + |
| 10. trehalose | + |
| 11. D-sorbitol | ± |
| 12. D-mannitol | + |
| 13. inositol | − |
| 14. glycerin | ± |
| 15. starch | + |

(17) pH in VP medium (medium 7)
pH 5.2
(18) Growth in a salt-containing medium (modified medium 1)
Not growing at 5%.
Not growing at 7%.
Not growing at 10%.
(19) Growth at a pH of 5.7 (medium 21)
Not growing.
(20) Formation of dihydroxyacetone (medium 22)
Whether the formation is negative or positive is not clear.
(21) Deamination of phenylalanine (medium 23)
Negative.
(22) Decomposition of casein (medium 24)
Negative.
(23) Decomposition of tyrosine (medium 25)
Negative.

Bacillus sp. KSM-521:
(a) Results of microscopic observation
Bacillus sp. KSM-521 has a size of the body of 0.6–0.8 micrometers × 1.0–2.0 micrometers, making a cylindrical or ellipsoidal endospore (0.4–0.8 micrometers × 1.0–2.0 micrometers) at the center of the body. It has flagella and is mobile. The Gram staining is positive. Not aciduric.
(b) Growing state in various media
(1) Meat broth agar plate culture (medium 1)
The growing state is good. The shape of the colonines is circular with a smooth surface and a smooth margin or a leaf-like form. The color tone of the colonies is light yellow, and the colonies are semi-transparent and glossy.
(2) Meat broth agar slant culture (medium 1)
Growing. The growing state is in a cloth-spread form and is light yellow and semi-transparent.
(3) Meat broth liquid culture (medium 2)
Growing but becoming turbid.
(4) Meat broth gelatin stab culture (medium 3)
Growing in the surface portions. The liquefaction of gelatin is recognized.
(5) Litmus milk culture (medium 4)
The liquefaction of milk is recognized. The litmus does not undergo any change in color.
(c) Physiological properties
(1) Reduction and denitrification reactions of nitrates (media 5, 6)
Both negative.
(2) MR test (medium 7)
Positive.
(3) VP test (medium 7)
Positive.
(4) Formation of indole (medium 8)
Negative.
(5) Formation of hydrogen sulfide (medium 9)
Negative.
(6) Hydrolysis of starch (medium 10)
Negative.
(7) Utility of citric acid (media 11, 12)
Positive in Christensen's medium, and whether negative or positive is not clear in Koser's medium.
(8) Utility of inorganic nitrogen sources (medium 13)
Negative with respect to the nitrate and ammonium salt.
(9) Formation of pigment (media 14, 15)
Positive.
(10) Urease (medium 16)
Negative.
(11) Oxidase (medium 17)
Whether negative or positive is not clear.
(12) Catalase (medium 18)
Positive.
(13) Temperature and pH ranges for growth (medium 2)

The temperature range for the growth is 10°–50° C. and an optimum temperature range is 20°–40° C.

The pH range for the growth is 5–10 and an optimum pH range is 6–10.

(14) Behavior to oxygen
Aerobic.
(15) O–F test (medium 19)
Oxidation.
(16) Formation of an acid and a gas from sugars (medium 20) (+: formed, −: not formed)

|  | Formation of acid | Formation of gas |
| --- | --- | --- |
| 1. L-arabinose | + | − |
| 2. D-xylose | + | − |
| 3. D-glucose | + | − |
| 4. D-mannose | + | − |
| 5. fructose | + | − |
| 6. D-galactose | + | − |
| 7. maltose | − | − |
| 8. sucrose | + | − |
| 9. lactose | − | − |
| 10. trehalose | + | − |
| 11. D-sorbitol | − | − |
| 12. D-mannitol | + | − |
| 13. Inositol | − | − |
| 14. glycerin | + | − |

-continued

| | Formation of acid | Formation of gas |
|---|---|---|
| 15. starch | — | — |

(17) pH in VP medium (medium 7)
pH 5.0
(18) Growth in a salt-containing medium (modified medium 1)
Growing in 5%, 7% and 10% NaCl.
(19) Growth at a pH of 5.7 (medium 21)
Growing.
(20) Formation of dihydroxyacetone (medium 22)
Negative.
(21) Deamidation of phenylalanine (medium 23)
Negative.
(22) Decomposition of casein (medium 24)
Positive.
(23) Decomposition of tyrosine (medium 25)
Negative.
Bacillus sp. KSM-522:
(a) Results of microscopic observation
Bacillus sp. KSM-522 has a size of the body of 0.5–0.8 micrometers × 1.0–2.0 micrometers, making an oval or a cylindrical endospore (0.5–0.8 micrometers × 1.0–1.2 micrometers) at the end of the center of the body. It has marginal flagelli and is mobile. The Gram staining is positive. Not aciduric.
(b) Growing state in various media
(1) Meat broth agar plate culture (medium 1)
Growing well. The shape of the colonies is circular with a coarse surface and a smooth or wavy margin. The color tone of the colonies is light yellow, and the colonies are semi-transparent with a resin hardness.
(2) Meat broth agar slant culture (medium 1)
Growing. The growing state is in a cloth-spread from and glossy, with milky white or light yellow in color and semi-transparency.
(3) Meat broth liquid culture (medium 2)
Growing and becoming turbid.
(4) Meat broth gelatin stab culture (medium 3)
Growing in the top surface portions. The liquefaction of gelatin is recognized.
(5) Litmus milk culture (medium 4)
The liquefaction of milk is recognized but the litmus does not undergo any change in color.
(c) Physiological properties
(1) Reduction and denitrification reactions of nitrates (media 5, 6)
Both negative.
(2) MR test (medium 7)
Positive.
(3) VP test (medium 7)
Positive.
(4) Formation of indole (medium 8)
Negative.
(5) Formation of hydrogen sulfide (medium 9)
Negative.
(6) Hydrolysis of starch (medium 10)
Negative.
(7) Utility of citric acid (media 11, 12)
Positive in Christensen's medium, but it is not clear in Koser's medium as to whether positive or negative.
(8) Utility of inorganic nitrogen sources (medium 13)
Negative with respect to the nitrate and ammonium salt.
(9) Formation of pigment (media 14, 15)
A water-soluble yellow pigment is formed in the King B medium.
(10) Urease (medium 16)
Negative.
(11) Oxidase (medium 17)
Whether negative or positive is not clear.
(12) Catalase (medium 18)
Positive.
(13) Temperature and pH ranges for growth (medium 2)
The temperature range for the growth is 10°–50° C. and an optimum temperature range is 20°–40° C.
The pH range for the growth is 5–10 and an optimum pH range is 6–10.
(14) Behavior to oxygen
Aerobic.
(15) O–F test (medium 19)
Oxidation.
(16) Formation of an acid and a gas from sugars (medium 20) (+: formed, —: not formed)

| | Formation of acid | Formation of gas |
|---|---|---|
| 1. L-arabinose | + | — |
| 2. D-xylose | + | — |
| 3. D-glucose | + | — |
| 4. D-mannose | + | — |
| 5. fructose | + | — |
| 6. D-galactose | + | — |
| 7. maltose | — | — |
| 8. sucrose | + | — |
| 9. lactose | — | — |
| 10. trehalose | + | — |
| 11. D-sorbitol | — | — |
| 12. D-mannitol | + | — |
| 13. Inositol | — | — |
| 14. glycerin | + | — |
| 15. starch | — | — |

(17) pH in VP medium (medium 7)
pH 5.0–5.2 (seventh day).
(18) Growth in a salt-containing medium (modified medium 1)
Growing in 5%, 7% and 10% NaCl.
(19) Growth at a pH of 5.7 (medium 21)
Growing.
(20) Decomposition of casein (medium 24)
Positive.
The above mycological properties are compared by reference to Bergey's Mannual of Determinative Bateriology, 8th edition and "The Genus Bacillus", in Agriculture Handbook No. 427 written by Ruth E. Gordon, Agricultural Research Service, U.S. Department of Agriculture, Washington D.C. (1973). As a result, it has been found that all the strains of the invention are considered to be microorganisms belonging to the genus Bacillus. The strains of the invention are apparently different from so-called alkalophilic microorganisms which have been recently reported by Horikoshi and Akiba ("Alkalophilic Microorganism", Japan Scientific Society Press (Tokyo), 1982). This is because the alkalophilic microorganisms grow in alkaline media having a pH not less than 8 and cannot grow up in a neutral or lower pH region, whereas the strains of the invention are able to grow in a weakly acidic to alkaline region (pH 5–10). Thus, the strains of the invention can be determined as ordinary microorganisms belong to the genus Bacillus, which grow under neutral conditions.
More detailed studies on the strains of the invention reveal that the species which is most analogous to the strain of Bacillus sp. KSM-580 may be *Bacillus licheniformis*. However, the comparison between the strain of the present invention and known strains belonging to the *Bacillus licheniformis* reveals that the KSM-580 strain is different from those known strains with respect to the reducibility of nitrates. In addition, the above known strains cannot produce at least alkaline cellulases, and thus the strain of the present invention is considered as a novel strain.

The species which is most analogous to Bacillus sp. KSM-425 may be *Bacillus circulans*. The comparison between known strains belonging to the circulantial and the strain of the invention demonstrates a difference in the capability of the hydrolysis of gelatin. Moreover, the above known strains do not produce alkaline cellulases. Thus, the KSM-425 is considered as a novel strain.

The species which is most analogous to the *Bacillus* sp. KSM-521 and KSM-522 strains may be *Bacillus pumilus*. However, known strains belonging to *Bacillus pumilus* do not produce at least alkaline cellulases. Thus, the KSM-521 and KSM-522 are considered as novel strains.

The present inventors deposited these strains to Fermentation Research Institute of Japan as follows.
Bacillus sp. KSM-580 as FERM BP-1511
Bacillus sp. KSM-425 as FERM BP-1505
Bacillus sp. KSM-521 as FERM BP-1507
Bacillus sp. KSM-522 as FERM BP-1512

For obtaining alkaline cellulases of the invention using these strains, the strain is inoculated into media and cultivated by a usual manner. The medium should preferably have suitable amounts of carbon and nitrogen sources to be utilized. These carbon and nitrogen sources are not critical. Examples of the nitrogen sources include corn gluten meal, soybean flour, corn steep liquor, casamino acid, yeast extract, Pharmamedia, sardine meal, meat extract, peptone, Hypro, Ajipower, corn soybean meal, coffee grounds, cotton seed oil cake, Cultivator, Amiflex, Ajipron, Zest, Ajix and the like. The carbon sources include, for example, plant fibers such as chaff, wheat-gluten bread, filter paper, ordinary papers, sawdust and the like, wasted theriac, invert sugar, CMC, Avicel, cellulose cotton, xylan, pectin and the like. In addition, utilizable carbon sources include, for example, arabinose, xylose, glucose, mannose, fructose, maltose, sucrose, lactose, trehalose, mannitol, sorbitol, inositol, glycerin, soluble starch and the like, and utilizable organic acids include, for example, citric acid, acetic acid and the like. Besides, phosphoric acid and inorganic salts such as of $Mg^{2+}$, $Ca^{2+}$, $Mn^{2+}$, $Zn^{2+}$, $Co^{2+}$, $Na^+$, $K^+$ and the like, and inorganic and organic trace nutrient sources may be appropriately added.

An intended alkaline cellulase can be collected from the thus obtained culture product and purified according to ordinary techniques of collecting and purifying enzymes. More particularly, the fungus bodies can be removed from a culture broth or solution by ordinary solid-liquid separation techniques such as centrifugal separation, filtration and the like, thereby obtaining a crude enzyme solution. This crude enzyme solution may be used as it is, or may be separated by salting-out, precipitation, ultrafiltration or the like to obtain a crude enzyme. The crude enzyme is subsequently purified by crystallization by any known methods to obtain a purified enzyme.

Among the thus obtained alkaline cellulases, the alkaline cellulase K-522 may be further separated into novel alkaline cellulases E-II and E-III. For the preparation of the alkaline cellulases E-II and E-III, the alkaline cellulase K-522 ia fractionally purified by a suitable combination of a hydroxyapatite chromatography, an ion exchange chromatography using DEAE-Sephadex (Pharmacia Inc.), DEAE-cellulose or the like, and a molecular sieve gel chromatography using Sephadex, Biogel (Bio-Rad Laboratories Inc.) and the like.

The thus obtained alkaline cellulases of the present invention have the following enzymatic properties. It will be noted that the enzymatic activity is measured according to the following procedure using the following buffer solutions.
pH 3-8 : McIlvaine buffer solution
pH 8-11 : glycine-sodium hydroxide buffer solution
pH 12-13: potassium chloride-sodium hydroxide buffer solution Enzymatic activity measurement:

(1) CMCase activity 0.1 ml of an enzyme solutin was added to 0.9 ml of a base solution comprising 10 mg of CMC (A-01L, by Sanyo Kokusaku Pulp Co., Ltd., Japan) and 100, $\mu$mols of each of the buffer solutions (McIlvaine, phosphoric acid, glycine-NaOH and the like), followed by reaction at 30° C. for 20 minutes. After completion of the reaction, (the resulting) reducing sugar was quantitatively determined according to the 3,5-dinitrosalicylic acid (DNS) method. More particularly, 1.0 ml of the DNS reagent was added to 1.0 ml of the reaction solution and heated at 100° C. for 5 minutes for color development. After cooling, 4.0 ml of deionized water was added for dilution. The diluted solution was subjected to colorimetry using a wavelength of 535 nm. The enzyme strength was expressed as one unit which was an amount of the enzyme sufficient to produce a reducing sugar corresponding to 1 $\mu$mol of glucose under the above conditions for 1 minute.

(2) Decomposition activity of PNPC

A suitable amount of CMCase was acted on 1.0 ml of a reaction solution containing 0.1 $\mu$mol of PNPC (Sigma Co., Ltd.) and 100 $\mu$mols of a phosphate buffer solution (pH 7.0) at 30° C., to which 0.3 ml of 1 M $Na_2CO_3$ and 1.7 ml of deionized water were added successively, followed by subjecting the resultant released pnitrophenol to colorimetry at 400 nm. The enzyme strength was expressed as one unit which was an amount of the enzyme sufficient to release 1 $\mu$mol of p-nitrophenol under the above conditions for 1 minute.

(3) Decomposition activities of Avicel, cellulose powder and filter paper

A suitable amount of an enzyme solution was added to 2.0 ml of a reaction solution containing 20 mg of Avicel (Merck, Inc.) and 200 $\mu$mols of a phosphate buffer solution (pH 7.0), followed by shaking for reaction at 30° C. at 250 r.p.m. After completion of the reaction, the solution was cooled and centrifugally separated (5° C., 3000 r.p.m., 20 minutes), and 1.0 ml of the resultant supernatant liquid was subjected to quantitative determination of reducing sugar according to the 3,5-dinitro-salicylic acid (DNS) method. The above procedure was repeated for a cellulose powder decomposition activity using cellulose powder (Toyo Filter Paper Co., Ltd.) and for a filter paper decomposition activity using a filter paper (filter paper for examination of the cellulase activity, Toyo No. 51-specific). The enzyme strength was expressed by one unit which was an amount of the enzyme sufficient to produce reducing sugar corresponding to 1 μmol of glucose under the above conditions for 1 minute.

(4) Cellobiase activity

A suitable amount of CMCase was acted on a 1.0 ml reaction solution containing 10 mg of cellobiose (Kanto Chem. Co., Ltd.) and 100 μmols of a phosphate buffer solution (pH 7.0) for an appropriate time, and then treated at 100° C. for 2 minutes, thereby inactivating the enzyme. Thereafter, the amount of the resultant glucose was measured by the Mutarotase-GOD method (glucose C-test, Wako Junyaku Ind. Co., Ltd.). The enzyme strength was expressed by one unit which was an amount of the enzyme sufficient to produce 2 μmols of glucose under the above conditions for 1 minute.

(Enzymatic properties)

Alkaline cellulase K-580

(1) Action

Acting well on cellulosic materials such as CMC, cellulose, filter paper, Avicel and the like and causing them to be dissolved, thereby producing reducing sugars such as glucose.

(2) Substrate specificity

This enzyme has activity not only on CMC, but also on cellulose powder, Avicel and filter paper (3) Working pH and optimum pH The working pH ranges very widely from 3 to 12.5 and the optimum pH is in the wide range of 7 to 10. In a range of 4.5 to 10.5, the relative activity is not less than 50% of the activity in the optimum pH range. Accordingly, this enzyme is believed to exhibit a satisfactory activity at the most alkaline side among known alkaline cellulases studied up to now (FIG. 1).

(4) pH Stability

Figure 2:
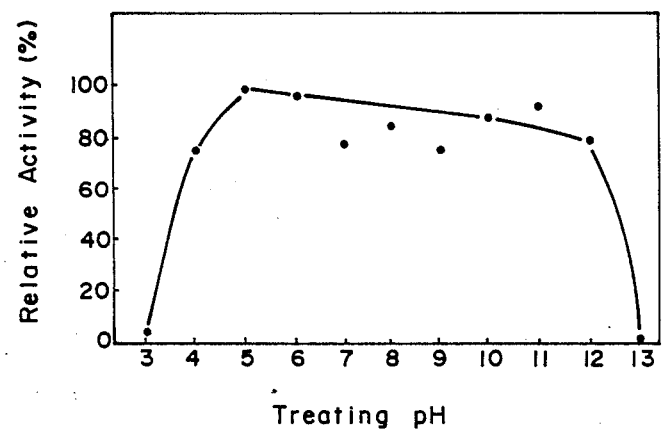
FIG. 2 is a graph showing the relation between a treating pH for the above enzyme and a residual activity.

The residual activity was measured after keeping the enzyme at different pHs at 30° C. for 1 hour to determine the pH stability. As a result, it was found that the enzyme was very stable and was not inactivated at a pH of 4.5 to 12. In a pH of from 3.5 to 12.5, an activity of about 50% or over was maintained. Thus, the present enzyme is satisfactorily stable in a high alkaline region (FIG. 2).

(5) Optimum temperature

Figure 3:
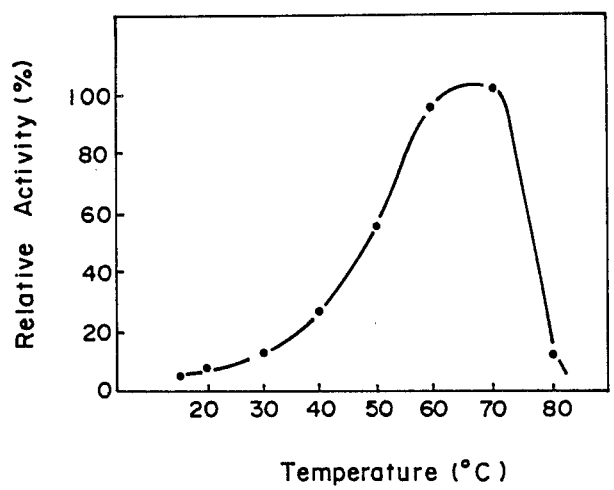
FIG. 3 is a graph showing the relation between a reaction temperature for the above enzyme and a relative activity.

The working temperature was in a wide range of from 15° to 80° C. and the optimum temperature was found to be 65° C. In a temperature range of from 50° to 75° C., the activity was 50% or higher of the activity at the optimum temperature (FIG. 3).

Figure 4:
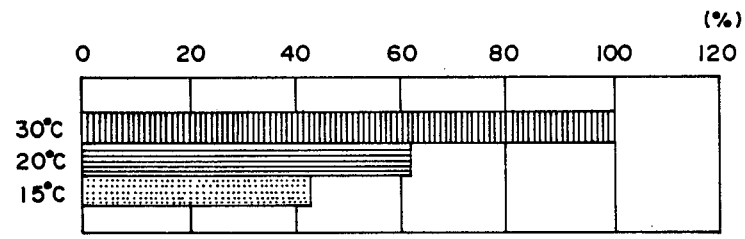
FIG. 4 is a graph showing activities at 15° C. and 20° C. when the activity of the above enzyme at 30° C. is taken as 100.

At 15° C., the activity was not less than 40% of the activity at 30° C. (FIG. 4).

(6) Temperature stability

Figure 5:
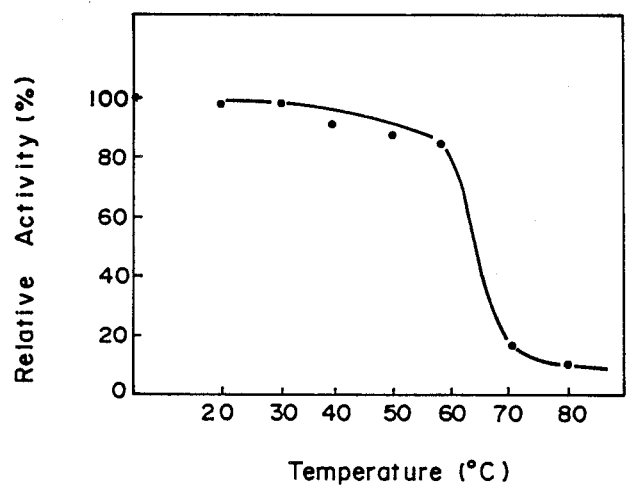
FIG. 5 is a graph showing the relation between a treating temperature for the above enzyme and a residual activity.

After treatment at the optimum pH for 30 minutes at different temperatures, the residual activity was measured. As a result, it was found that it was stable at 55° C. and a residual activity of about 50% was obtained at 65° C. (FIG. 5).

(7) Molecular weight

The molecular weight of the present enzyme was measured according to the gel filtration method using Sephadex G-100, with the result that it was about 18,000 and 50,000.

(8) Influences of metal ions

The present enzyme was subjected to determination of influences of various metal ions ($Al^{3+}$, $Fe^{3+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentratin of $K^+$ or $Na^+$ was 50 mM and the concentration of other ions was 1 mM). As a result, it was found that the activity was inhibited with $Hg^{2+}$, but was more enhanced with $Ba^{2+}$, $Ca^{2+}$, $Co^{2+}$ and $Cd^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C. for 15 minutes and subjected to the measurement of activity. As a result, the activity was not inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, sodium tripolyphosphate, zeolite and citric acid were allowed to coexist at the time of the measurement of the activity, with the result that no inhibition was recognized.

Alkaline cellulase K-425

(1) Action

Action well on cellulosic materials such as CMC, cellulose, filter paper, Avicel and the like and causing them to be dissolved, thereby producing reducing sugars such as glucose.

(2) Substrate specificity

This enzyme has activity not only on CMC, but also on cellulose powder, Avicel, filter paper, PNPC and cellobiose.

(3) Working pH and optimum pH

Figure 6:
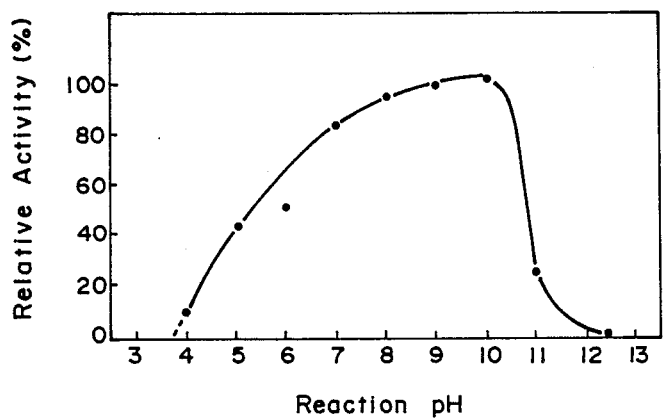
FIG. 6 is a graph showing the relation between a pH for the enzyme reaction of alkaline cellulase K-425 and a relative activity.

The working pH ranges very widely from 3.5 to 12.5 and the optimum pH is in the wide range of 8 to 10. In a range of 5.5 to 10.5, the relative activity is not less than 50% of the activity in the optimum pH range. Accordingly, this enzyme is believed to exhibit a satisfactory activity at the most alkaline side among known alkaline cellulases studied up to now (FIG. 6).

(4) pH Stability

Figure 7:
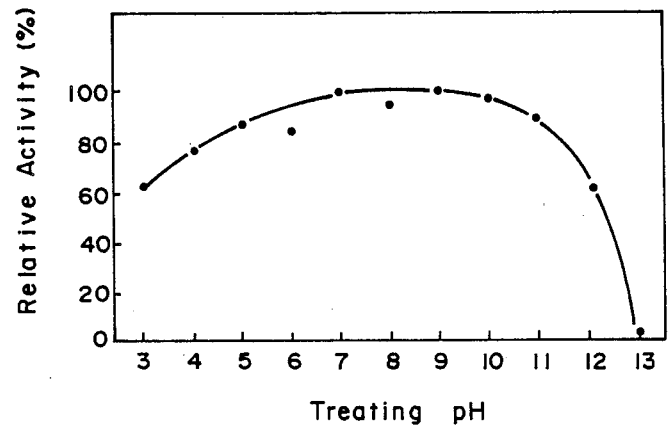
FIG. 7 is a graph showing a treating pH for K-425 and a residual activity.

The residual activity was measured after keeping the enzyme at different pHs at 30° C. for 1 hour to determine the pH stability. As a result, it was found that the enzyme was very stable and was not inactivated at a pH of 5 to 11. In a pH of from 3 to 12, an activity of about 50% or over was maintained. Thus, the present enzyme is satisfactorily stable in a high alkaline region (FIG. 7).

(5) Optimum temperature

Figure 8:
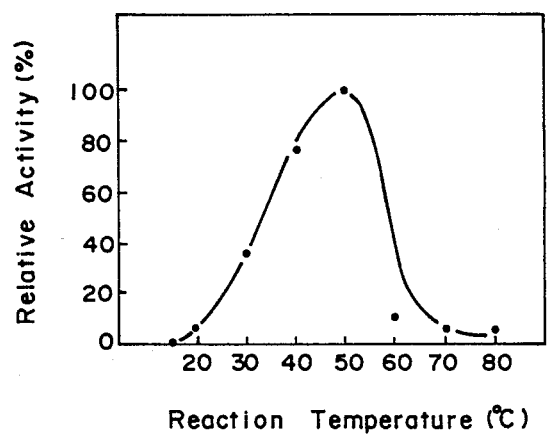
FIG. 8 is a graph showing a reaction temperature for K-425 and a relative activity.

The working temperature was in a wide range of from 15° to 75° C. and the optimum temperature was found to be 50° C. In a temperature range of from 35° to 55° C., the activity was 50% or higher of the activity at the optimum temperature (FIG. 8).

(6) Temperature stability

Figure 9:
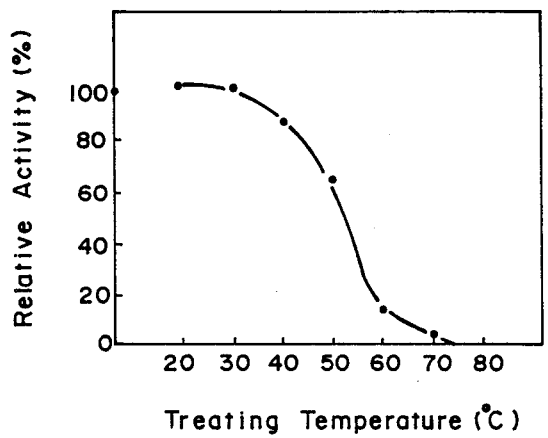
FIG. 9 is a graph showing a treating temperature for K-425 and a residual activity.

After treatment at the optimum pH for 30 minutes at different temperatures, the residual activity was measured. As a result, it was found that it was stable at 30° C. and a residual activity of about 50% was obtained at 50° C. (FIG. 9).

(7) Molecular weight

The molecular weight of the present enzyme was measured according to the gel filtration method using Sephadex G-100, with the result that it was about 35,000.

(8) Influences of metal ions

The present enzyme was subjected to determination of influences of various metal ions ($Al^{3+}$, $Fe^{3+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of $K^+$ or $Na^+$ was 50 mM and the concentration of the other ions was 1 mM). As a result, it was found that the activity was inhibited by $Hg^{2+}$ and $Ba^{2+}$, but was more enhanced by $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C. for 15 minutes and subjected to the measurement of activity As a result, the activity was not inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, sodium tripolyphosphate, zeolite and citric acid were allowed to coexist at the time of the measurement of the activity, with the result that no inhibition was recognized.

Alkaline cellulase K-521

(1) Action

Acting well on cellulosic materials such as CMC, cellulose powder, filter paper, Avicel and the like and causing them to be dissolved, thereby producing reducing sugars such as glucose.

(2) Substrate specificity

This enzyme has activity not only on CMC, but also on cellulose powder, Avicel, filter paper, p-nitrophenyl cellobioside and cellobiose.

(3) Working pH and optimum pH

Figure 10:
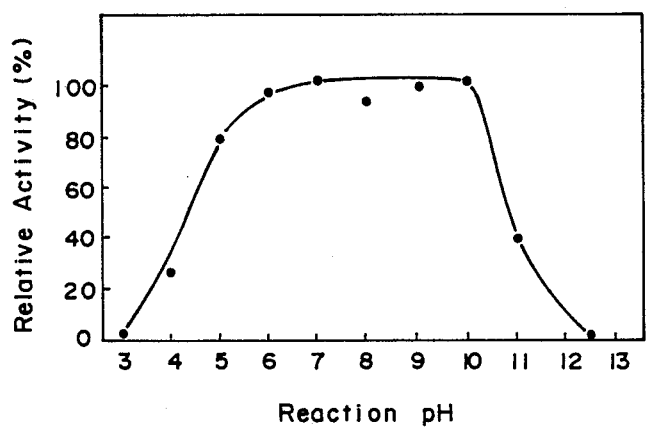
FIG. 10 is a graph showing the relation between a pH for the enzyme reaction of alkaline cellulase K-521 and a relative activity.

The working pH ranges very widely from 3 to 12.5 and the optimum pH is in the wide range of 7 to 10. In a range of 4.5 to 10.5, the relative activity is not less than 50% of the activity in the optimum pH range. Accordingly, this enzyme is believed to exhibit a satisfactory activity at the most alkaline side among known alkaline cellulases studies up to now (FIG. 10).

(4) pH stability

Figure 11:
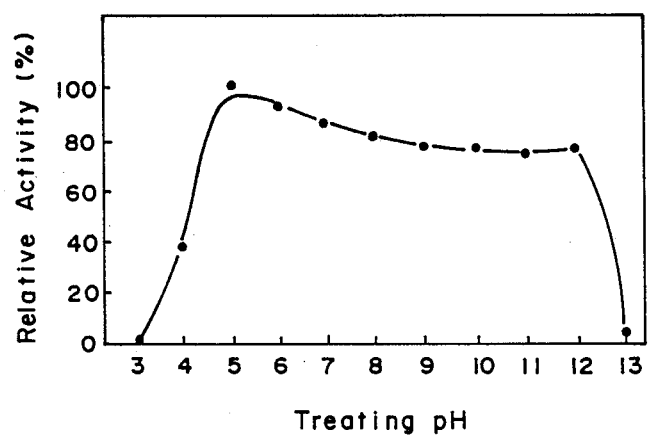
FIG. 11 is a graph showing the relation between a treating pH for K-521 and a residual activity.

The residual activity was measured after keeping the enzyme at different pHs at 30° C. for 1 hour to determine the pH stability. As a result, it was found that the enzyme was very stable and was not inactivated at a pH of 5 to 12. In a pH of from 4.5 to 12.5, an activity of about 50% or over was maintained. Thus, the present enzyme is satisfactorily stable in a high alkaline region (FIG. 11).

(5) Optimum temperature

Figure 12:
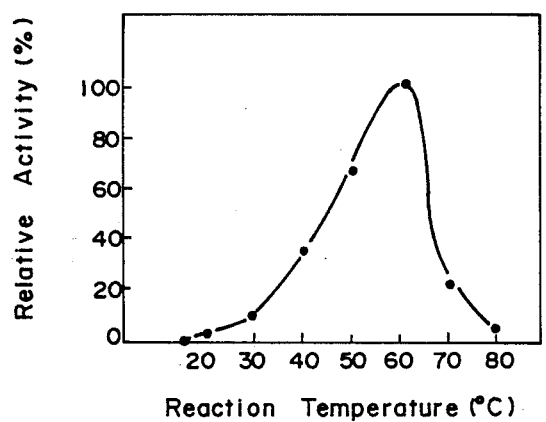
FIG. 12 is a graph showing the relation between a reaction temperature for K-521 and a relative activity.

The working temperature was in a wide range of from 15° to 80° C. and the optimum temperature was found to be 60° C. In a temperature range of from 45° to 65° C., the activity was 50% or higher of the activity at the optimum temperature (FIG. 12).

(6) Temperature stability

Figure 13:
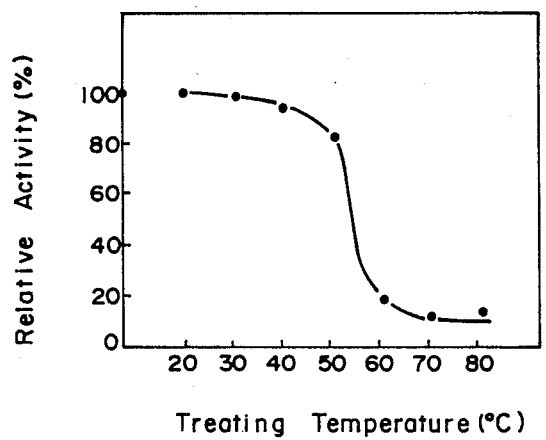
FIG. 13 is a graph showing the relation between a treating temperature for K-521 and a relative activity.

After treatment at the optimum pH for 30 minutes at different temperature, the residual activity was measured. As a result, it was found that it was stable at 40° C. and a residual activity of about 50% was obtained at 55° C. (FIG. 13).

(7) Molecular weight

The molecular weight of the present enzyme was measured according to the gel filtration method using Sephadex G-100, with the result that it was about 31,000.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentratin of $K^+$ or $Na^+$ was 50 mM and the concentration of the other ions was 1 mM). As a result, it was found that the activity was inhibited by $Hg^{2+}$, but was more enhanced by $Ca^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C. for 15 minutes and subjected to the measurement of activity As a result, the activity was rarely inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, sodium tripolyphosphate, zeolite and citric acid were allowed to coexist at the time of the measurement of the activity, with the result that little inhibition was recognized.

Alkaline cellulase K-522

(1) Action

Acting well on cellulosic materials such as CMC, cellulose powder, filter paper, Avicel and the like and causing them to be dissolved, thereby producing reducing sugars such as glucose.

(2) Substrate specificity

This enzyme has activity not only on CMC, but also on cellulose powder, phosphoric acid-swollen cellulose, alkali-swollen cellulose, Avicel, filter paper and PNPC.

(3) Working pH and optimum pH

Figure 14:
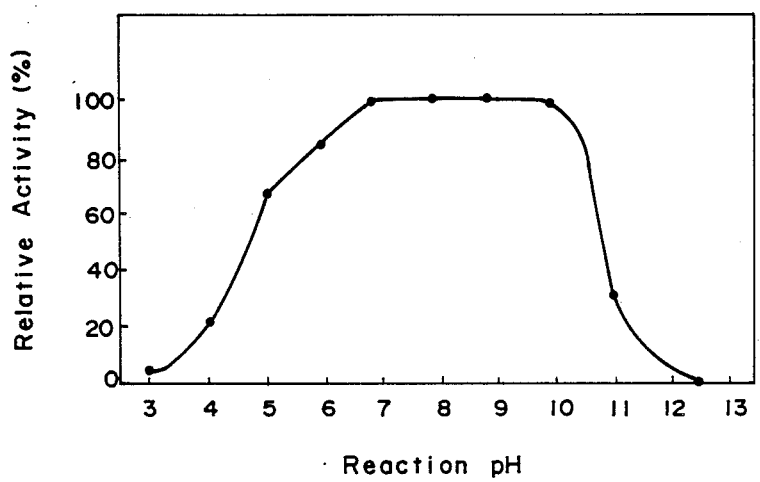
FIG. 14 is a graph showing the relation between a pH for the enzyme reaction of alkaline cellulase K-522 and a relative activity.

The working pH ranges very widely from 3 to 12.5 and the optimum pH is in the side range of 7 to 10. In a range of 4.5 to 10.5, the relative activity is not less than 50% of the activity in the optimum pH range. Accordingly, this enzyme is believed to exhibit a satisfactory activity at the most alkaline side among known alkaline cellulases studied up to now (FIG. 14).

(4) pH stability

Figure 15:
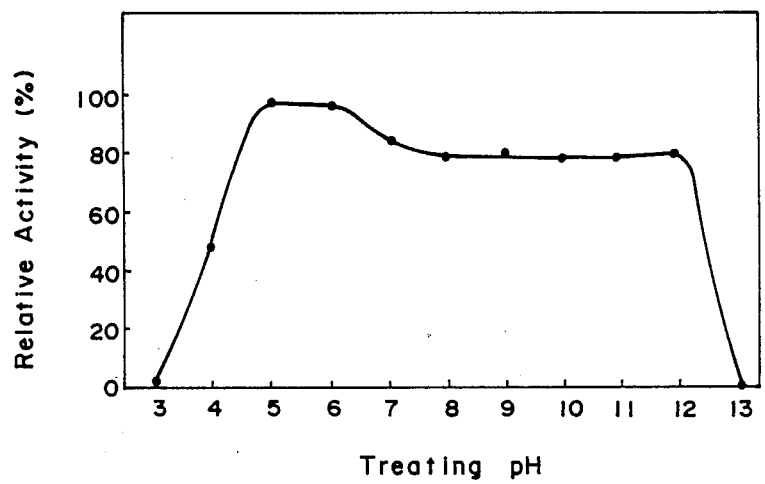
FIG. 15 is a graph showing the relation between a treating pH for K-522 and a residual activity.

The residual activity was measured after keeping the enzyme at different pHs at 30° C. for 1 hour to determine the pH stability. As a result, it was found that the enzyme was very stable and was not inactivated at a pH of 5 to 12. In a pH of from 4.5 to 12.5, an activity of about 50% or over was maintained. Thus, the present enzyme is satisfactorily stable in a high alkaline region (FIG. 15).

(5) Optimum temperature

Figure 16:
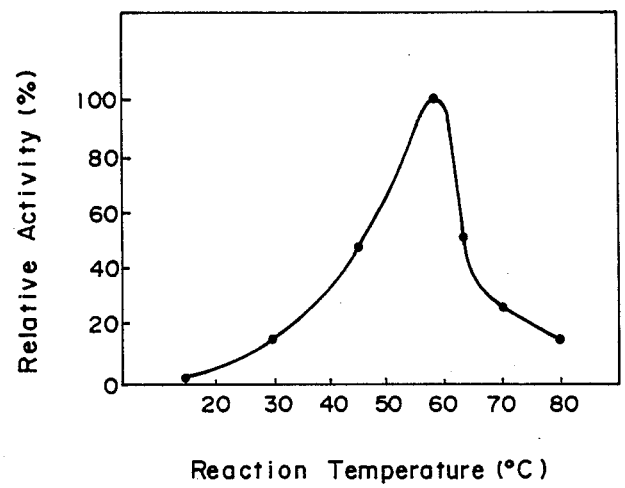
FIG. 16 is a graph showing the relation between a reaction temperature for K-522 and a relative activity.

The working temperature was in a wide range of from 15° to 80° C. and the optimum temperature was found to be 60° C. In a temperature range of from 45° to 65° C., the activity was 50% or higher of the activity at the optimum temperature (FIG. 16).

(6) Temperature stability

Figure 17:
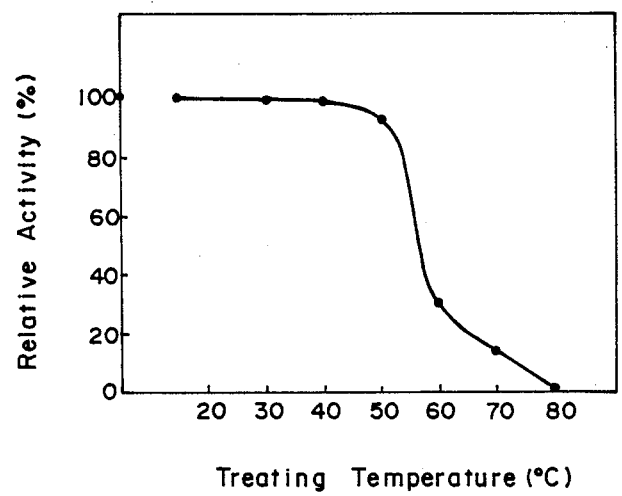
FIG. 17 is a graph showing the relation between a treating temperature for K-522 and a residual activity.

After treatment at the optimum pH for 30 minutes at different temperatures, the residual activity was measured. As a result, it was found that it was stable at 40° C. and a residual activity of about 50% was obtained at 55° C. (FIG. 17).

(7) Molecular weight

The molecular weight of the present enzyme was measured according to the gel filtration method using Bio-Gel P-150 (Bio-Rad Laboratories Co., Ltd.), with the result that it was about 35,000.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentratin of $K^+$ or $Na^+$ was 50 mM and the concentration of the other ions was 1 mM). As a result, it was found that the activity was inhibited by $Hg^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C. for 15 minutes and subjected to the measurement of activity. As a result, the activity was rarely inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, sodium tripolyphosphate, zeolite and citric acid were allowed to coexist at the time of the measurement of the activity, with the result that little inhibition was recognized.

Alkaline cellulase E-II (1) Action

Acting well on cellulosic materials such as CMC and phosphoric acid-swollen cellulose and causing them to be dissolved, thereby producing reducing sugars such as glucose.

(2) Substrate specificity

This enzyme has activity not only a main activity on CMC, but also an activity on cellulose swollen with phosphoric acid, which is about 0.4% of CMCase activity. Moreover, it has a slight decomposition activity on xylan, inulin and lichenan, but has little activity on cellulose powder, Avicel, filter paper, PNPC and cellobiose.

(3) Working pH and optimum pH

Figure 18:
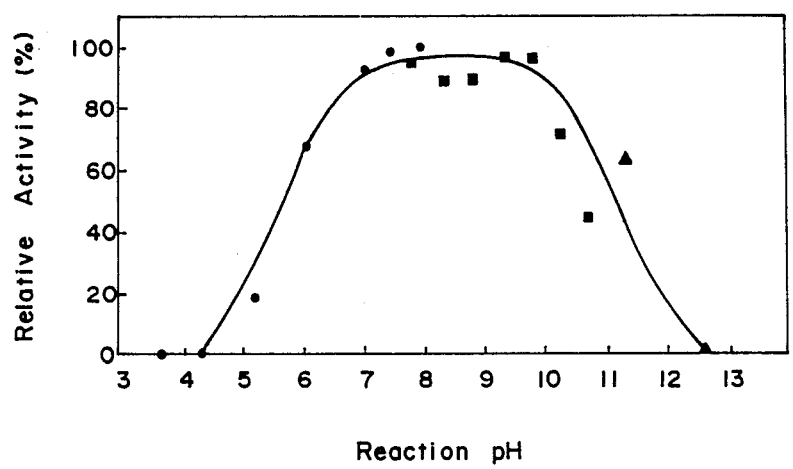
FIG. 18 is a graph showing the relation between a pH for the enzyme reaction of alkaline cellulase E-II and a relative activity.

The working pH ranges very widely from 4 to 12.5 and the optimum pH is in the wide range of 7 to 10. In a range of 5.5 to 11, the relative activity is not less than 50% of the activity in the optimum pH range. Accordingly, this enzyme is believed to exhibit a satisfactory activity at the most alkaline side among known alkaline cellulases studied upto now (FIG. 18).

(4) pH stability

Figure 19:
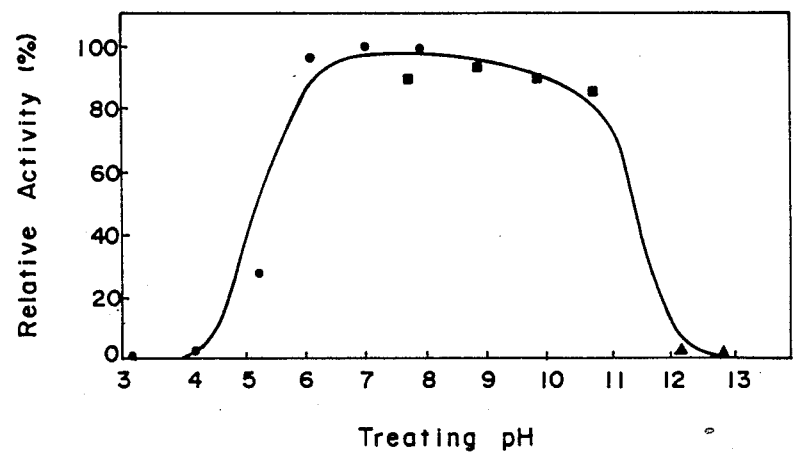
FIG. 19 is a graph showing the relation between a treating pH for E-II and a residual activity.

The residual activity was measured after keeping the enzyme at different pHs at 0° C. for 24 hours to determine the pH stability. As a result, it was found that the enzyme was very stable and was not inactivated at a pH of 6 to 11. In a pH of from 5.5 to 11.5, an activity of about 50% or over was maintained. Thus, the present enzyme is satisfactorily stable in a high alkaline region (FIG. 19).

(5) Optimum temperature

Figure 20:
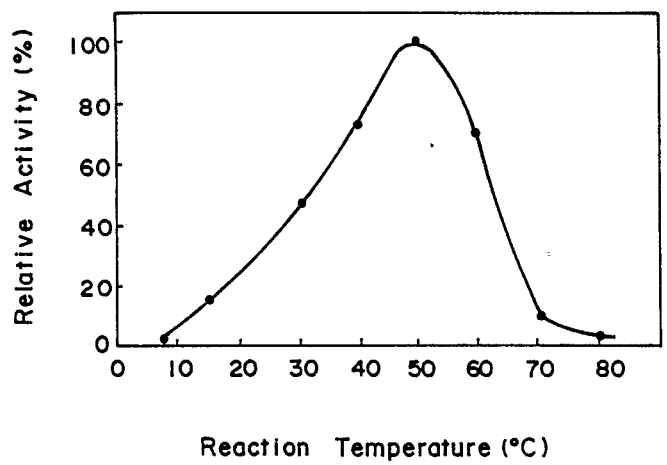
FIG. 20 is a graph showing the relation between a reaction temperature for E-II and a relative activity.

The working temperature was in a wide range of from 10° to 80° C. and the optimum temperature was found to be 50° C. In a temperature range of from 30° to 65° C., the activity was 50% or higher of the activity at the optimum temperature (FIG. 20).

(6) Temperature stability

Figure 21:
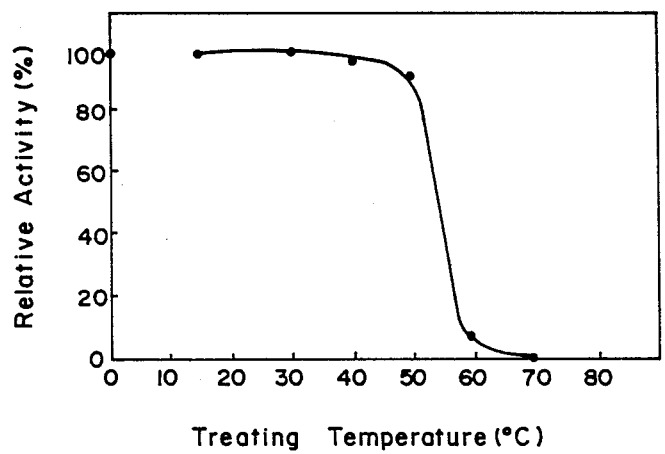
FIG. 21 is a graph showing the relation between a treating temperature for E-II and a residual activity.

After treatment at a pH of 7 for 30 minutes at different temperatures, the residual activity was measured. As a result, it was found that it was stable at 50° C. and a residual activity of about 50% was obtained at 55° C. (FIG. 21).

(7) Molecular weight

Figure 23:
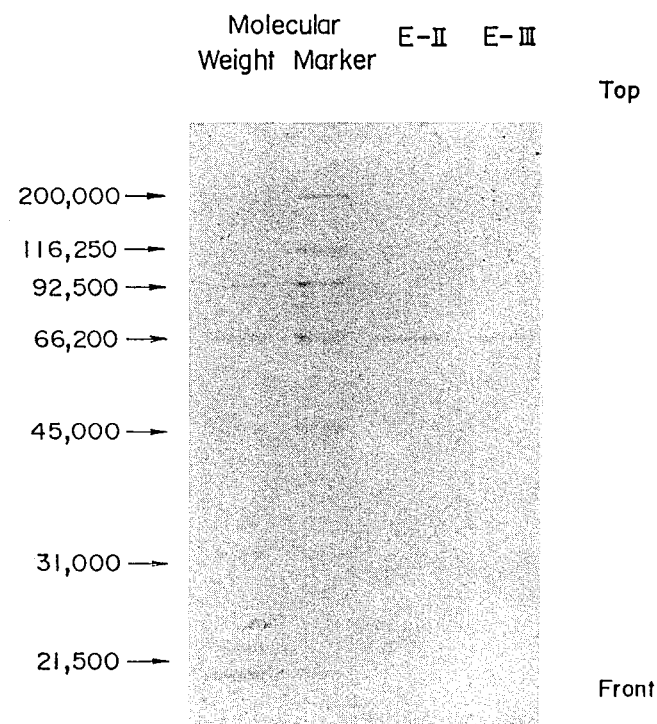
FIG. 23 is a chart showing the results of SDS/polyacrylamide gel electrophoresis of alkaline cellulases E-II and E-III.

The molecular weight of the present enzyme was measured according to the gel filtration method using Bio-Gel P-100 (Bio-Rad Laboratories Co., Ltd.), with the result that it was about 34,000. With an SDS-polyacrylamide gel electrophoresis, the molecular weight was about 61,000 (FIG. 23).

(8) Influences of metal ions

The present enzyme was subjected to determination of influences of various metal ions The present enzyme was subjected to ($Al^{3+}$, $Fe^{3+}$, $Ba^{2+}$, $Ca^{2+}$, $Cd^{2+}$, $Co^{2+}$, $Cu^{2+}$, $Fe^{2+}$, $Hg^{2+}$, $Mn^{2+}$, $Mg^{2+}$, $Ni^{2+}$, $Pb^{2+}$, $Zn^{2+}$, $Li^+$, $K^+$ and $Na^+$) by permitting the ions to coexist at the time of the measurement of the activity (in which the concentration of $K^+$ or $Na^+$ was 50 mM and the concentration of the other ions was 1 mM). As a result, it was found that the activity was inhibited with $Hg^{2+}$ and enhanced with $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was subjected to the measurement of the activity in 0.05% of a surface active agent. As a result, any significant influences of the surface active agents were recognized as shown in Table 1.

TABLE 1

| Surface Active Agent | Residual Activity (%) |
|---|---|
| nil | 100 |
| LAS | 79 |

TABLE 1-continued

| Surface Active Agent | Residual Activity (%) |
| --- | --- |
| AS | 108 |
| ES | 98 |
| AOS | 100 |
| alpha-SFE | 129 |
| SAS | 93 |
| Soap | 100 |
| Polyoxyethylene secondary alkyl ether | 86 |

In addition, the inhibition of the activity was not recognized when using sodium dodecylsulfate which was a potential detergent.

(10) Proteinase resistance

Proteinases for detergents such as, for example API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases as shown in Table 2.

TABLE 2

| Proteinase | Residual Activity (%) |
| --- | --- |
| nil | 100 |
| Alkalase | 111 |
| API-21 | 115 |
| Maxatase | 120 |

(11) Influences of chelating agents

Chelating agents such as EDTA, EGTA, sodium tripolyphosphate, zeolite and citric acid were allowed to coexist at the time of the measurement of the activity, with the result that little inhibition was recognized.

(12) UV absorption spectrum

Figure 24:
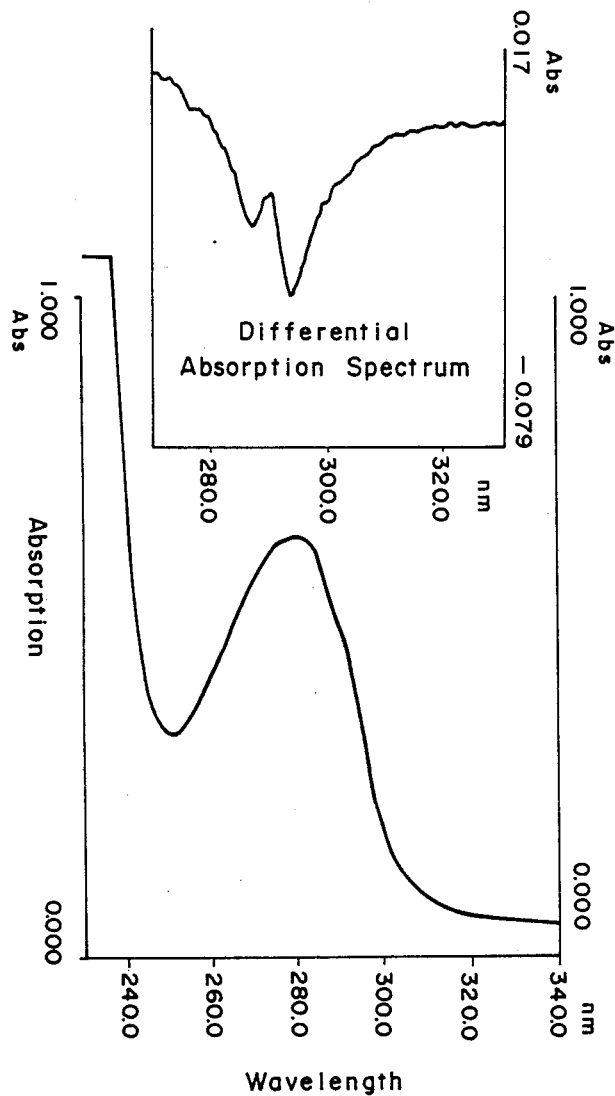
FIG. 24 is a UV absorption spectrum of alkaline cellulase E-II.

The present enzyme was subjected to measurement of UV absorption spectrum. As a result, it was found that it had a maximum absorption at about 280 nm with a shoulder absorption being shown at 290 nm by a differential absorption spectrum (FIG. 24).

Alkaline cellulase E-III (1) Action

Acting well on celluloses such as CMC and phosphoric acid-swollen cellulose and causing them to be dissolved, thereby producing reducing sugars such as glucose.

(2) Substrate specificity

This enzyme has not only a main activity on CMC, but also an activity on cellulose swollen with about 4.5% phosphoric acid. Moreover, it has a slight decomposition activity on xylan, lichenan and the like, but has little activity on cellulose powder, Avicel, filter paper, PNPC and cellobiose.

(3) Working pH and optimum pH

Figure 25:
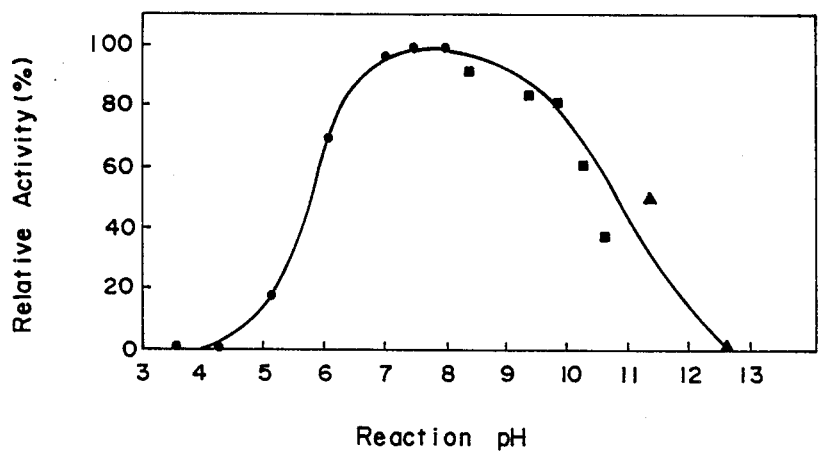
FIG. 25 is a graph showing the relation between a pH for the enzyme reaction of alkaline cellulase E-III and a relative activity.

The working pH ranges very widely from 4 to 12.5 and the optimum pH is in the wide range of 7 to 9. In a range of 6 to 10.5, the relative activity is not less than 50% of the activity in the optimum pH range Accordingly, this enzyme is believed to exhibit a satisfactory activity at the most alkaline side among known alkaline cellulases studies up to now (FIG. 25).

(4) pH stability

Figure 26:
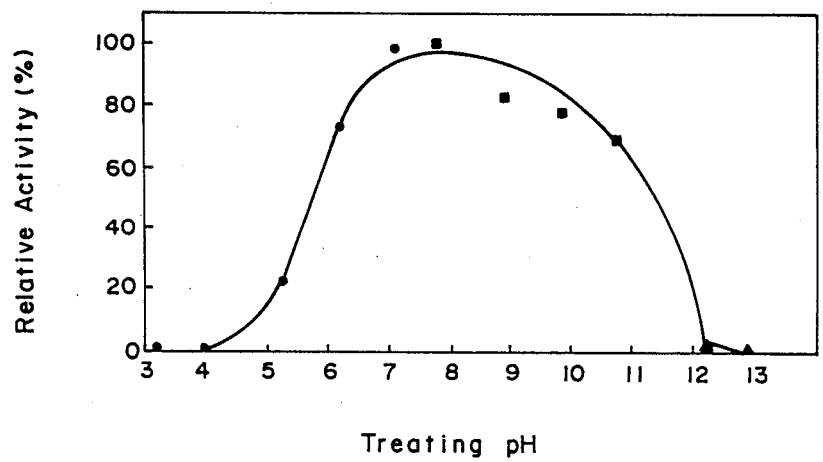
FIG. 26 is a graph showing the relation between a treating pH for E-III and a residual activity.

The residual activity was measured after keeping the enzyme at different pHs at 5° C. for 24 hours to determine the pH stability. As a result, it was found that the enzyme was very stable and was not inactivated at a pH of 6 to 10. In a pH of from 5.7 to 11.5, an activity of about 50% or over was maintained. Thus, the present enzyme is satisfactorily stable in a high alkaline region (FIG. 26).

(5) Optimum temperature

Figure 27:
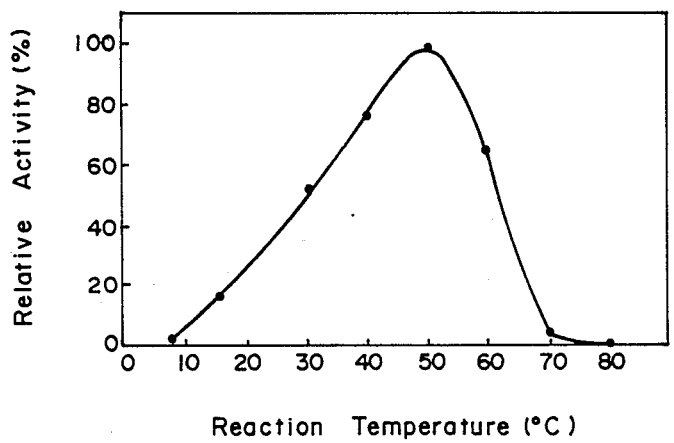
FIG. 27 is a graph showing the relation between a reactin temperature of E-III and a relative activity.

The working temperature was in a wide range of from 10° to 80° C. and the optimum temperature was found to be 50° C. In a temperature range of from 30° to 62° C., the activity was 50% or higher of the activity at the optimum temperature (FIG. 27).

(6) Temperature stability

Figure 28:
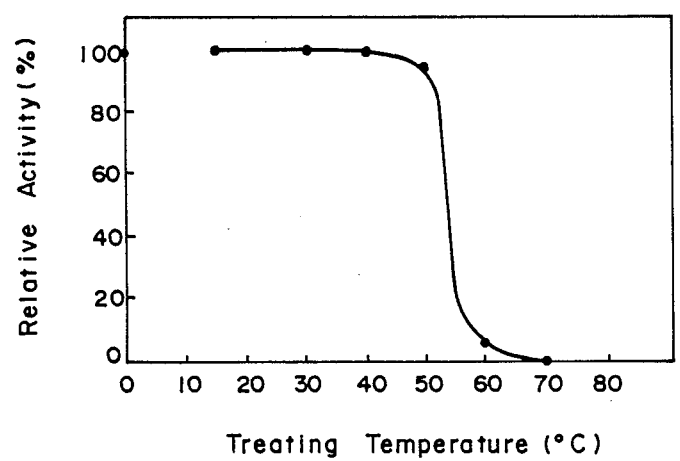
FIG. 28 is a graph showing the relation between a treating temperature for E-III and a residual activity.

After treatment at a pH of 7 for 30 minutes at different temperatures, the residual activity was measured. As a result, it was found that it was stable at 50° C. and a residual activity of about 50% was obtained at 55° C. (FIG. 28).

(7) Molecular weight

The molecular weight of the present enzyme was measured according to the gel filtration method using Bio-Gel P-100 (Bio-Rad Laboratories Co., Ltd.), with the result that it was about 35,000. With an SDS-polyacrylamide gel electrophoresis, the molecular weight was about 61,000 (FIG. 23).

(8) Influences of metal ions

The present enzyme was subjected to determination of influences of various metal ions ($Al^{3+}$, $Fe^{3+}$, $Ca^{2+}$, $Co^{2+}$, $Cr^{2+}$, $Cu^{2+}$, $Fe^{2+}$, $Hg^{2+}$, $Mg^{2+}$, $Mn^{2+}$, $Ni^{2+}$, $Pb^{2+}$, $Zn^{2+}$, $K^+$, and $Na^+$) by permitting the ions to coexist at the time of the measurement of the activity (in which the concentration of $K^+$ or $Na^+$ was 50 mM and the concentration of the other ions was 1 mM). As a result, it was found that the activity was inhibited with $Hg^{2+}$ and enhanced with $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was subjected to the measurement of the activity in 0.05% of a surface active agent. As a result, any significant influences of the surface active agents were recognized as shown in Table 3.

TABLE 3

| Surface Active Agent | Residual Activity (%) |
| --- | --- |
| nil | 100 |
| LAS | 78 |
| AS | 107 |
| ES | 100 |
| AOS | 101 |
| alpha-SFE | 104 |
| SAS | 97 |
| Soap | 101 |
| Polyoxyethylene secondary alkyl ether | 96 |

In addition, the inhibition of the activity was not recognized when using sodium dodecylsulfate which was a potential detergent.

(10) Proteinase resistance

Proteinases for detergents such as, for example API-21 (Showa Denko Co., Ltd.), Maxatase (Gist Co., Ltd.) and Alkalase (Novo Co., Ltd.), were allowed to coexist (0.1 mg/ml) at the time of the measurement of the activity to determine their influences. It was found that the enzyme had a high resistance to these proteinases as shown in Table 4.

TABLE 4

| Proteinase | Residual Activity (%) |
| --- | --- |
| nil | 100 |
| Alkalase | 94 |
| API-21 | 106 |
| Maxatase | 103 |

(11) Influences of chelating agents

Chelating agents such as EDTA, EGTA, sodium tripolyphosphate, zeolite and citric acid were allowed to coexist at the time of the measurement of the activity, with the result that little inhibition was recognized.

(12) UV absorption sepctrum

Figure 29:
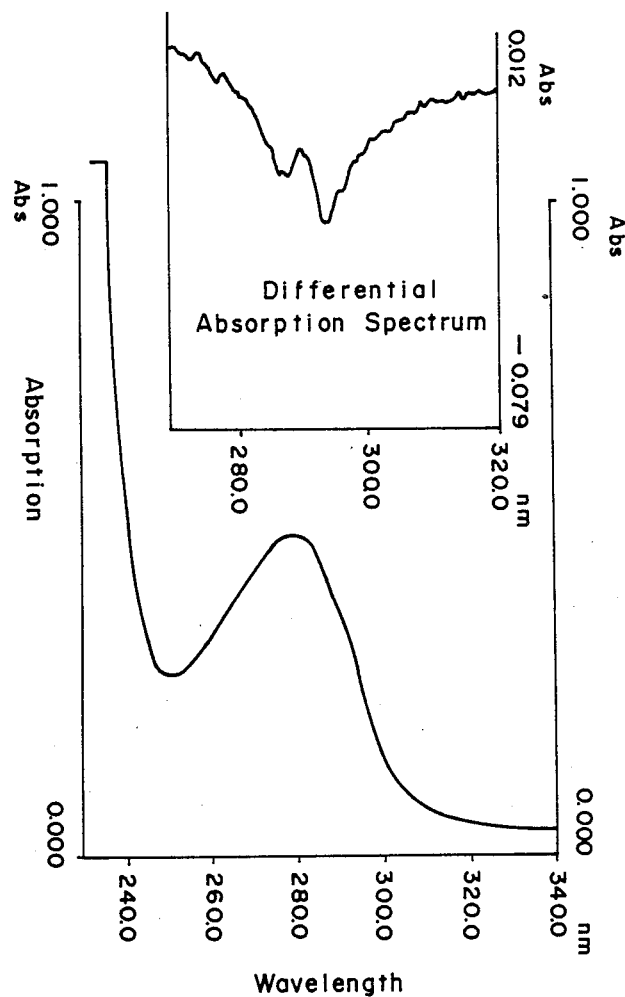
FIG. 29 is a UV absorption spectrum of alkaline cellulase E-III.

The present enzyme was subjected to measurement of a UV absorption spectrum. As a result, it was found that it had a maximum absorption at about 280 nm with a shoulder absorption being shown at 290 nm by a differential absorption spectrum (FIG. 29).

The alkaline cellulases of the invention have an optimum pH at a higher level (pH 10) than known alkaline cellulases and are very stable over a wide pH range. For example, alkaline cellulase K-580 has, in a wide pH range of from 4.5 to 10.5, an activity not less than 50% of the activity at the optimum pH, and is very stable in a pH range of from 4.5 to 12. Alkaline cellulase K-425 has also, in a wide pH range of from 5.5 to 10.5, an activity of not less than 50% of the activity at the optimum oH, and is very stable in a pH range of from 5 to 11. Moreover, alkaline cellulases K-521 and K-522 have, respectively, an optimum pH in a wide range of from 7.0 to 10 and is very stable in a wide range.

The alkaline cellulases E-II and E-III derived from the alkaline cellulase K-522 have, respectively, higher optimum pHs (of 10 and 9) than known alkaline cellulases. In addition, they have, respectively, wide optimum pH ranges of 7.0 to 10 and 7.0 to 9 are very stable in such wide ranges.

These alkaline cellulases are rarely inhibited with ingredients ordinarily fomulated in detergents such as, for example, surface active agents, proteinases, chelating agents and the like. Accordingly, the present enzymes can be conveniently used in detergent compositions.

The microorganisms of the invention grow under neutral conditions, so that it is possible to industrially produce alkaline cellulases more easily than in the case using alkalophilic strains.

The present invention is described in more detail by way of the following examples.

EXAMPLE 1

A spoonful (about 0.5 g) of the soil obtained at Ichikai-machi, Haga-gun, Tochigi-ken, Japan was suspended in a sterilized physiological saline solution and thermally treated at 80° C. for 10 minutes. The supernatant liquid of the thermally treated solution was appropriately diluted and applied to an agar medium for isolation (medium 1), followed by cultivation at 30° C. for 3 days to form colonies. Colonies around which a transparent zone was formed on the basis of the dissolution of CMC were selected to collect CMCase-producing microorganisms belonging to the genus Bacillus. The thus collected microorganisms were inoculated into a liquid medium as medium 2 and subjected to shaking culture at 30° C. for 3 days. After completion of the culture, a centrifugally separated supernatant liquid was obtained and subjected to measurement of the CMCase activity in a pH range of from 3 to 13 and also to screening of alkaline cellulase-producing microorganisms belonging to the genus Bacillus.

By the above procedure, there could be obtained Bacillus sp. KSM-580 strain, Bacillus sp. KSM-425 strain, and Bacillus sp. KSM-521 strain.

| Medium 1 | |
| --- | --- |
| CMC | 2% |
| Polypeptone | 0.5 |
| Yeast extract | 0.05 |
| $KH_2PO_4$ | 0.1 |
| $Na_2HPO_4 \cdot 12H_2O$ | 0.25 |
| $MgSO_4 \cdot 7H_2O$ | 0.02 |
| Agar | 0.75 |
| pH 6.8 | |
| Medium 2 | |
| CMC | 1% |
| Polypeptone | 1 |
| Yeast extract | 0.5 |
| $KH_2PO_4$ | 0.1 |
| $Na_2HPO_4 \cdot 12H_2O$ | 0.25 |
| $MgSO_4 \cdot 7H_2O$ | 0.02 |
| pH 6.8 | |

EXAMPLE 2

The Bacillus sp. KSM-580 strain obtained in Example 1 was inoculated into the liquid medium 2 of Example 1, followed by shaking culture at 30° C. for 3 days. After completion of the culture, the bacillus cells were centrifugally removed to obtain a crude enzyme solution. 3 liters of ethanol was added to 1 liter of the crude enzyme solution in dry ice/ethanol and the resultant precipitate was centrifugally removed, followed by freeze-drying to obtain 11 g of alkaline cellulase K-580 (specific activity* 33 units/g) as a dry powder.

* The enzyme activity was a value at a pH of 9.

EXAMPLE 3

The Bacillus sp. KSM-580 strain was inoculated into a medium of the same composition as the liquid medium 2 of Example 1 except that CMC was replaced by sucrose and polypeptone was replaced by 7% of a corn steep liquor (CSL), followed by shaking culture at 30° C. for 2 days. The resultant culture product was subjected to centrifugal separation and the resulting supernatant liquid was, in turn, subjected to measurement of the CMCase activity. As a result, the activity was 60 units/liter.

EXAMPLE 4

The Bacillus sp. KSM-425 strain obtained in Example 1 was inoculated into the liquid medium 2 of Example 1 and shake-cultured at 30° C. for 3 days. After completion of the culture, the bacillus cells were centrifugally removed to obtain a crude enzyme solution. 3 liters of ethanol was added to 1 liter of the crude enzyme solution in dry ice/ethanol, and the resultant precipitate was centrifugally removed and freeze-dried to obtain 10 g of alkaline cellulase K-425 (specific activity* 10 units/g) as a dry powder.

* The enzyme activity was a value measured at a pH of 9.

EXAMPLE 5

The Bacillus sp. KSM-425 strain was inoculated into a medium of the same composition as the liquid medium 2 of Example 1 except that CMC was replaced by sucrose and polypeptone was replaced by 7% CSL, followed by shaking culture at 30° C. for 2 days. The culture product was centrifugally separated and the resultant supernatant liquid was subjected to measurement of the CMCase activity. As a result, the activity was 160 units/liter.

EXAMPLE 6

The Bacillus sp. KSM-521 strain obtained in Example 1 was inoculated into the liquid medium 2 of Example 1 and shake-cultured at 30° C. for 3 days. After completion of the culture, the bacillus cells were centrifugally removed to obtain a crude enzyme solution 3 liters of ethanol was added to 1 liter of the crude enzyme solution in dry ice/ethanol, and the resultant precipitated was centrifugally separated and freezedried to obtain 9 g of alkaline cellulase K-521 (specific activity* 20 units/g) as a dry powder.

* The enzyme activity was a value measured at a pH of 9 herein and hereinafter.

EXAMPLE 7

The KSM-521 strain was inoculated into a medium of the same composition as the liquid medium 2 of Example 1 except that CMC was replaced by 1% sucrose and polypeptone was replaced by 7% CSL, followed by shaking culture at 30° C. for 2 days. The culture product was centrifugally separated and the resultant supernatant liquid was subjected to measurement of the CMCase activity. As a result, it was found that the activity was 100 units/liter.

EXAMPLE 8

A spoonful (0.5 g) of the soil obtained at Nikko-shi, Tochigi-ken, Japan was taken and suspended in a sterilized saline solution, followed by repeating the procedure of Example 1, thereby obtaining KSM-522 strain (FERM BP-1512) of the invention.

EXAMPLE 9

The Bacillus sp. KSM-522 strain obtained in Example 8 was inoculated into the liquid medium of Example 1 and shake-cultured at 30° C. for 3 days. After the culture, the bacillus cells were centrifugally separated to obtain a crude solution 3 liters of ethanol was added to 1 liter of the crude enzyme solution in dry ice/ethanol, and the resultant precipitate was centrifugally separated and freeze-dried to obtain 8 g of alkaline cellulase K-522 (specific activity* 23 units/g) as a dry powder.

* The enzyme activity was a value measured at a pH of 9.

EXAMPLE 10

The KSM-522 strain was inoculated into a medium of the same composition as the liquid medium 2 of Example 1 except that CMC was replaced by 1% sucrose and polypeptone was replaced by 7% CSL, followed by shaking culture at a temperature of 30° C. for 2 days. The culture product was centrifugally separated and the resultant supernatant liquid was subjected to measurement of the CMCase activity, with the result that the activity was 150 units/liter.

EXAMPLE 11

5 liters of the supernatant obtained in Example 10 was purified according to the following procedure.
(1) Concentration by ultrafiltration (Amicon Co., Ltd., fractionating molecular weight of 10,000).
(2) Treatment with Streptomycin.
(3) Chromatography using DEAE-BioGel A (Bio-Rad Laboratories Co., Ltd.).
(4) Chromatography using hydroxyapatite (Wako Junyaku Ind. Co., Ltd.).
(5) Chromatography using DEAE-BioGel A.
(6) Chromatography using DEAE-BioGel A.

Figure 22:
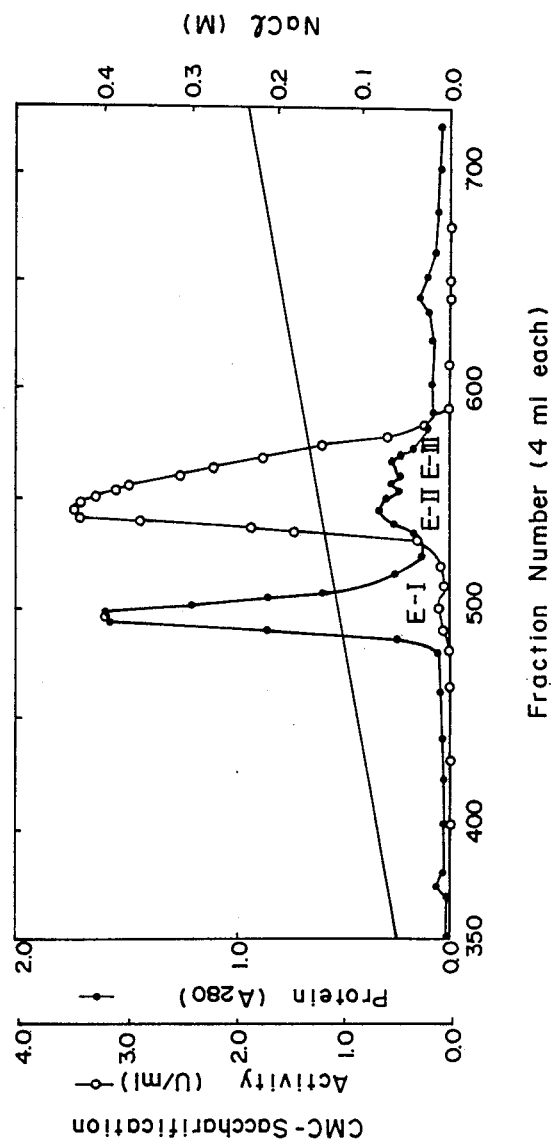
FIG. 22 is an ion-exchange chromatogram obtained in the third purification step.

In the third step of the above procedure, the enzyme was adsorbed in a column having a size of 3.2×33 cm (equilibrated with a 10mM phosphate buffer solution wiht a pH of 7), followed by linearly increasing the concentration of NaCl from 0 to 300 mM for eluation. This permitted neutral cellulase E-I, alkaline cellulase E-II and alkaline cellulase E-III to be eluted in this order (FIG. 22). The fractions of from 533 to 580 from which the fraction of E-I had been removed were collected and further purified. In the fourth step, the fractions were adsorbed in a column with a size of 2.5×13 cm (equilibrated with a 10 mM phosphate buffer solution with a pH of 7), after which the concentration of the phosphate was icreased from 10 to 200 mM linearly to obtain an alkaline cellulase fraction (a mixture of E-II and E-III). In the fifth step, the procedure of (3) was repeated (in which the concentration of NaCl was increased linearly from 70 to 200 mM) to collect alkaline cellulase E-II with the residue being subjected to the sixth step. The sixth step was effected similar to (3) or (5) but the gradient in concentration of NaCl was further lowered by changing from 90 to 150 mM for elution, therby isolating the alkaline cellulase E-III. The thus purified alkaline cellulases E-II and E-III were subjected to polyacrylamide electrophoresis by a usual manner and further to Coomassie Brilliant Blue dyeing and silver staining, by which it was confirmed that the respective cellulases gave a single band.

EXAMPLE 12

The alkaline cellulases E-II and E-III obtained in Example 11 were subjected to SDS-polyacrylamide gel electrophoresis by a usual manner. The results are shown in FIG. 23. From the results, it was found that the alkaline cellulases E-II and E-III each had a molecular weight of about 61,000.

According to the gel filtration method using Bio-Gel P-100, the alkaline cellulase E-II had a molecular weight of about 34,000 and the alkaline cellulase E-III had a molecular weight of about 35,000.

What is claimed is:

1. A substantially pure alkaline cellulase enzyme K-580 isolated from Bacillus species KSM-580 having the following enzymatic properties:
    (1) Action:
    acting well on cellulosic materials including carboxymethyl cellulose, cellulose, filter paper and microcrystalline cellulose and causing them to be dissolved, thereby forming reducing sugars such as glucose;
    (2) Substrate specificity:
    having activity on carboxymethyl cellulose, cellulose powder, microcrystalline cellulose and filter paper;
    (3) Working pH and optimum pH:
    a working pH range from 3 to 12.5 and an optimum pH from 7 to 10 with a relative activity of not less than 50% of the activity at an optimum pH being shown in the range of 4.5 to 10.5;
    (4) pH stability:
    very stable and not inactivated at a pH of 4.5 to 12 and an activity of not less than about 50% being maintained at a pH of 3.5 to 12.5;
    (5) Optimum temperature:

a working temperature in a wide range of 15 to 80° C. and an optimum temperature of 65° C.; in the range of 50° to 75° C., the activity is not less than 50% of the activity at the optimum temperature;

(6) Molecular weight;

peaks of the molecular weight are at about 18,000 and about 50,000 (when determined by gel filtration);

(7) Influences of metal ions;

inhibited by $Hg^{2+}$ and activated by $Ba^{2+}$, $Ca^{2+}$, $Co^{2+}$ and $Cd^{2+}$;

(8) Influences of surface active agents:

sodium linear alkylbenzenesulfonates, sodium alkylsulfates, sodium polyoxyethylene alkylsulfates, sodium alpha-olefin sulfonates, sodium alpha-sulfonated aliphatic acid esters, sodium alkylsulfonates, soaps and polyoxyethylene secondary alkyl ethers rarely inhibit the activity;

(9) Proteinase resistance;

resistant to proteinases;

(10) Influences of chelating agents:

ethylenediamine tetraacetic acid, ethyleneglycolbis-(beta-aminoethylether)-N,N,N',N"-tetraacetic acid, citric acid, sodium tripolyphosphate and zeolite do not inhibit the activity.

2. A substantially pure alkaline cellulase enzyme K-425 isolated from Bacillus species KSM-425 having the following enzymatic properties:

(1) Action:

acting well on cellulosic materials including carboxymethyl cellulose, cellulose, filter paper and microcrystalline cellulose and causing them to be dissolved, thereby forming reducing sugars such as glucose;

(2) Substrate specificity:

having activity on carboxymethyl cellulose, cellulose powder, microcrystalline cellulose, filter paper, p-nitrophenyl cellobioside and cellobiose;

(3) Working pH and optimum pH:

a working pH range of from 3.5 to 12.5 and an optimum pH of from 8 to 10 with a relative activity of not less than 50% of the activity at an optimum pH being shown in the range of 5.5 to 10.5;

(4) pH stability:

very stable and not inactivated at a pH of 5 to 11 and an activity of not less than about 50% being maintained at a pH of 3 to 12;

(5) Optimum temperature;

a working temperature in a wide range of 15 to 75° C. and an optimum temperature is 50° C.; in the range of 35° to 55° C., the activity is not less than 50% of the activity at the optimum temperature;

(6) Molecular weight:

about 35,000 (when determined by gel filtration);

(7) Influences of metal ions:

inhibited by $Hg^{2+}$ and $Ba^{2+}$ and activated by $Co^{2+}$;

(8) Influences of surface active agents:

sodium linear alkylbenzenesulfonates, sodium alkylsulfates, sodium polyoxyethylene alkylsulfates, sodium alpha-olefin sulfonates, sodium alpha-sulfonated aliphatic acid esters, sodium alkylsulfonates, soap and polyoxyethylene secondary alkyl ethers rarely inhibit the activity;

(9) Proteinase resistance:

resistant to proteinases;

(10) Influences of chelating agents:

ethylenediamine tetraacetic acid, ethyleneglycolbis-(beta-aminoethylether)-N,N,N',N"-tetraacetic acid, citric acid, sodium tripolyphosphate and zeolite do not inhibit the activity.

3. A substantially pure alkaline cellulase enzyme K-521 isolated from Bacillus species KSM-521 having the following enzymatic properties:

(1) Action:

acting well on cellulosic materials including carboxymethyl cellulose, cellulose, filter paper and microcrystalline cellulose and causing them to be dissolved, thereby forming reducing sugars such as glucose;

(2) Substrate specificity:

having activity on carboxymethyl cellulose, cellulose powder, microcrystalline cellulose, filter paper, p-nitrophenyl cellobiose and cellobiose;

(3) Working pH and optimum pH:

a working pH range of from 3 to 12.5 and an optimum pH of from 7 to 10 with a relative activity of not less than 50% of the activity at an optimum pH being shown in the range of 4.5 to 10.5;

(4) pH stability:

very stable and not inactivated at a pH of 5 to 12 and an activity of not less than about 50% being maintained at a pH of 4.5 to 12.5;

(5) Optimum temperature:

a working temperature in a wide range of 15 to 80° C. and an optimum temperature is 60° C.; in the range of 45° to 65° C., the activity is not less than 50% of the activity at the optimum temperature;

(6) Molecular weight:

about 31,000 (when determined by gel filtration);

(7) Influences of metal ions:

inhibited by $Hg^{2+}$ and activated by $Ca^{2+}$;

(8) Influences of surface active agents:

sodium linear alkylbenzenesulfonates, sodium alkylsulfates, sodium polyoxyethylene alkylsulfates, sodium alpha-olefin sulfonates, sodium alpha-sulfonated aliphatic acid esters, sodium alkylsulfonates, soaps and polyoxyethylene secondary alkyl ethers rarely inhibit the activity;

(9) Proteinase resistance:

resistant to proteinases;

(10) Influences of chelating agents:

ethylenediamine tetraacetic acid, ethyleneglycolbis-(beta-aminoethylether)-N,N,N',N"-tetraacetic acid, citric acid, sodium tripolyphosphate and zeolite do not inhibit the activity.

4. A substantially pure alkaline cellulase enzyme K-522 isolated from Bacillus KSM-522 having the following enzymatic properties:

(1) Action:

acting well on cellulosic materials including carboxymethyl cellulose, cellulose, filter paper and microcrystalline cellulose and causing them to be dissolved, thereby forming reducing sugars such as glucose;

(2) Substrate specificity:

having activity on carboxymethyl cellulose, cellulose powder, phosphoric acid-swollen cellulose, alkali-swollen cellulose, microcrystalline cellulose, filter paper, and p-nitrophenyl cellobioside;

(3) Working pH and optimum pH:

a working pH range of from 3 to 12.5 and an optimum pH of from 7 to 10 with a relative activity of not less than 50% of the activity at an optimum pH being shown in the range of 4.5 to 10.5;

(4) pH stability:

very stable and not inactivated at a pH of 5 to 12 and an activity of not less than about 50% being maintained at a pH of 4.5 to 12.5;

(5) Optimum temperature:

a working temperature in a wide range of 15° to 80° C. and an optimum temperature of 60° C.; in the range of 45° to 65° C., the activity is not less than 50% of the activity at the optimum temperature;

(6) Molecular weight:

about 35,000 (when determined by gel filtration);

(7) Influences of metal ions:

inhibited by $Hg^{2+}$;

(8) Influences of surface active agents:

sodium linear alkylbenzenesulfonates, sodium alkylsulfates, sodium polyoxyethylene alkylsulfates, sodium alpha-olefin sulfonates, sodium alpha-sulfonated aliphatic acid esters, sodium alkylsulfonates, soaps and polyoxyethylene secondary alkyl ethers rarely inhibit the activity;

(9) Proteinase resistance:

resistant to proteinases;

(10) Influences of chelating agents:

ethylenediamine tetraacetic acid, ethyleneglycolbis-(beta-aminoethylether)-N,N,N',N'''-tetraacetic acid, citric acid, sodium tripolyphosphate and zeolite do not inhibit the activity.

5. A biologically pure culture of Bacillus sp. KSM-580 deposited as FERM BP-1511 which is capable of producing the alkaline cellulase K-580 of claim 1.

6. A biologically pure culture of Bacillus sp. KSM-425 deposited as FERM BP-1505 which is capable of producing the alkaline cellulase K-425 of claim 2.

7. A biologically pure culture of Bacillus sp. KSM-521 deposited as FERM BP-1507 which is capable of producing the alkaline cellulase K-521 of claim 3.

8. A biologically pure culture of Bacillus sp. KSM-522 deposited as FERM BP-1512 which is capable of producing the alkaline cellulase K-522 of claim 4.

9. A process for producing an alkaline cellulase enzyme having an optimum pH not less than pH 8 which comprises cultivating an alkaline cellulase enzyme producing bacterium selected from the group consisting of Bacillus species KSM-580 deposited as FERM BP-1511, Bacillus species KSM-425 deposited as FERM BP-1505, Bacillus species KSM-521 deposited as FERM BP-1507 and Bacillus species KSM-522 deposited as FERM BP-1512, which is capable of growing in a neutral medium, in a neutral medium and collecting the alkaline cellulase enzyme having an optimum pH not less than pH 8 from the resulting culture product.

10. The process according to claim 9, wherein said alkaline cellulase has the following enzymatic properties:

(1) optimum pH: 8–10, (2) inhibited in the presence of $Hg^{2+}$, (3) rarely inhibited with proteinases, surface active agents and chelating agents, (4) the carboxymethyl cellulose decomposing activity (Cx activity) being a main activity with additional filter paper disintegrating activity and microcrystalline cellulose activity ($C_1$ activity).

11. The process according to claim 9, wherein the bacterium is an alkaline cellulase K-580-producing bacterium Bacillus sp. KSM-580 deposited as FERM BP-1511.

12. The process according to claim 9, wherein the bacterium is an alkaline cellulase K-425-producing bacterium Bacillus sp. KSM-425 deposited as FERM BP-1505.

13. The process according to claim 9, wherein the bacterium is an alkaline cellulase K-521-producing bacterium Bacillus sp. KSM-521 and deposited as FERM BP-1507.

14. The process according to claim 9, wherein the bacterium is an alkaline cellulase K-522-producing bacterium Bacillus sp. KSM-522 deposited as FERM BP-1512.

* * * * *

UNITED STATES PATENT AND TRADEMARK OFFICE
CERTIFICATE OF CORRECTION

PATENT NO. : 4,962,030

DATED : OCTOBER 9, 1990

INVENTOR(S) : SHUJI KAWAI ET AL

It is certified that error appears in the above-identified patent and that said Letters Patent is hereby corrected as shown below:

Column 28, line 34, delete "and".

Signed and Sealed this

Tenth Day of August, 1993

Attest:

MICHAEL K. KIRK

Attesting Officer     Acting Commissioner of Patents and Trademarks